(12) United States Patent
Saracione

(10) Patent No.: US 6,716,220 B2
(45) Date of Patent: *Apr. 6, 2004

(54) STEREOTAXIC HOLDERS, STEREOTAXIC ALIGNMENT SYSTEMS COMPRISING SAME, AND METHODS FOR USING SAME

(75) Inventor: Joseph Saracione, Gresham, OR (US)

(73) Assignee: David Kopf Instruments, Tujunga, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/217,884

(22) Filed: Aug. 12, 2002

(65) Prior Publication Data

US 2003/0125753 A1 Jul. 3, 2003

Related U.S. Application Data

(63) Continuation of application No. 09/514,008, filed on Feb. 25, 2000, now abandoned.
(60) Provisional application No. 60/122,484, filed on Feb. 26, 1999.

(51) Int. Cl.[7] ............................................. A61B 19/00
(52) U.S. Cl. ....................................... 606/130; 119/752
(58) Field of Search ........................ 606/130; 119/712, 119/722, 753, 756; 5/607, 608, 610, 611; 128/897; 269/55, 56, 71

(56) References Cited

U.S. PATENT DOCUMENTS

| | | | | |
|---|---|---|---|---|
| 3,364,352 A | * | 1/1968 | Fry et al. ................... 378/163 |
| 4,256,112 A | * | 3/1981 | Kopf et al. ................. 606/130 |
| 4,583,537 A | * | 4/1986 | Derechinsky et al. ....... 606/130 |
| 4,875,478 A | * | 10/1989 | Chen ......................... 600/429 |
| 5,030,223 A | * | 7/1991 | Anderson et al. ........... 606/130 |
| 5,147,358 A | * | 9/1992 | Remmler ...................... 606/57 |
| 5,160,337 A | * | 11/1992 | Cosman ..................... 606/130 |
| 5,601,570 A | * | 2/1997 | Altmann et al. ............ 606/130 |
| 5,933,887 A | * | 8/1999 | Strange et al. ................ 5/600 |
| 6,258,103 B1 | * | 7/2001 | Saracione ................... 606/130 |

* cited by examiner

Primary Examiner—Eduardo C. Robert
(74) Attorney, Agent, or Firm—Klarquist Sparkman, LLP

(57) ABSTRACT

Apparatus and methods are disclosed for holding a subject body (or body portion, generally termed "body") at a desired stereotaxic orientation relative to a known reference point, in three-dimensional space, where a reference X-axis, a reference Y-axis, and a reference Z-axis mutually intersect. The reference point can be co-positioned with a target point on or in the subject body so as to place the body in a reference position used in a corresponding anatomical atlas or other locational index. With the body so positioned, a probe or other tool can be inserted into the body to a desired locus with high accuracy (in hitting the desired locus) and with high precision (from one animal to the next). The methods and apparatus have especial utility in surgical and diagnostic interventions, including such interventions involving the central nervous system encased in surrounding skull or the like.

71 Claims, 17 Drawing Sheets

STEREOTAXIC HOLDERS, STEREOTAXIC ALIGNMENT SYSTEMS COMPRISING SAME, AND METHODS FOR USING SAME

CROSS REFERENCE TO RELATED APPLICATIONS

This application is a continuation of and claims the benefit of U.S. application Ser. No. 09/514,008, filed Feb. 25, 2000 now abandoned which claims the benefit of Provisional application No. 60/122,484 filed Feb. 26, 1999.

FIELD OF THE INVENTION

This invention pertains to instrument systems and methods for positioning the body, or a portion of the body, of a surgical subject (or other "body" as defined herein) at a predetermined three-dimensional position in space. The systems and methods have especial utility for surgery, diagnostic intervention, and research involving the subject's brain or other anatomical structure located in the interior of the subject's body, wherein the brain or other anatomical structure has a buried locus of interest that normally is obscured by overlying structure.

BACKGROUND OF THE INVENTION

In research and surgery of animals including small animals such as rats and mice, it can be extremely difficult to locate a terminus of a probe, electrode, micropipette, or other implement (herein generally termed a "probe") at a particular location within the subject's body without having to remove overlying structure and the like to permit direct observation of placement of the probe. This problem is especially critical in brain research involving the placement of a probe at a desired locus deep within a living subject's brain inside the surrounding skull.

To aid researchers in locating various anatomical structures in the brains of research animals such as mice, rats, cats, dogs, and primates, respective so-called brain atlases are often consulted. A brain atlas provides three-dimensional coordinates for the structures, normally using a Cartesian (rectangular) coordinate system, relative to one or more accessible anatomical features. (For example, for mice and rats, the usual reference feature on the skull is bregma, which is a point of meeting of the coronal and sagittal sutures. A second reference feature that is sometimes used in connection with bregma is lambda, which is located posteriorly of bregma and is a point of meeting of the lambdoidal and sagittal sutures. The sagittal suture connecting bregma and lambda is regarded generally as representing a sagittal mid-line of the skull.) However, despite the existence of such information, current apparatus and methods used to place an introduced probe are notoriously inaccurate with individual subjects and from one subject to another in a population of subjects. Such inaccuracy is a substantial problem because it results in unintentionally mis-positioned probes and other tools, which causes misleading research data and wasted animal resources.

Stereotaxic apparatus are known in the art for positioning a subject's head for brain research. For a small animal such as a mouse or rat, the head is held immobile by externally applied structures such as ear bars and a nose clamp providing a "three-point" holding system. As an example, reference is made to U.S. Pat. No. 5,601,570 to Altmann et al.

All known prior-art apparatus have various substantial shortcomings. For example, the Altmann et al. apparatus is inherently incapable of positioning a subject's head, in three-dimensional space, in a manner providing a high level of confidence that a probe inserted from outside the skull will "hit" a desired locus within the brain. More specifically, the Altmann et al. apparatus does not allow the researcher, intending to probe a living brain of a research animal, to position a particular animal's head in a manner providing reliably accurate insertion and placement of the probe to desired three-dimensional coordinates in the brain. The Altmann apparatus also exhibits poor precision of placements of a probe at a desired locus in each animal in a population of animals. Consequently, the researcher must conduct a series of "pilot" studies, followed by histological confirmations, to compare actual probe results with desired results (e.g., to compare actual hit loci with desired hit loci based on information in a brain atlas). Such studies using conventional apparatus usually produce data exhibiting wide variations that often are attributed wrongly to biological variations among individual animals in a population, strains, ages of animals, and so on. As the pilot studies progress, the coordinates provided by a conventional apparatus are adjusted gradually to compensate for the variation and to improve the hit rate. Unfortunately, such studies are time-consuming and costly to perform, and require substantially increased numbers of animals to conduct a particular experiment. Conventional instruments simply do not allow the researcher to differentiate between the many sources of error. Furthermore, even with adjustments to the apparatus based on the pilot studies, hit rates remain disappointingly low, resulting in inconclusive research.

As noted above, individual animals (even of the same strain) exhibit substantial variation, one animal to the next, in morphology of body structures such as the skull. If positioning of the body or body structure is guided, according to the prior art, solely on the basis of external features (e.g., positions of ear holes relative to each other and to the snout), this variation usually results in excessive variation in probe placement at target loci within the brain.

SUMMARY OF THE INVENTION

In view of the shortcomings of the prior art summarized above, the present invention provides, inter alia, apparatus and methods for positioning the body, or portion of the body (such as the skull and its contents), of a research subject accurately in three-dimensional space. (As used herein, the term "body" can be an entire body such as an entire mouse or rat, or a portion of an entire body.) To achieve such positioning, the body is held in a holder configured to hold the body immobile in a desired position. The holder, in turn, is mounted in a manner allowing any of various motions in three-dimensional space required to achieve the desired positioning.

According to a first aspect of the invention, stereotaxic holders are provided for holding a body at a position in three-dimensional space. A representative embodiment of such a holder comprises a frame, an X-axis shift mechanism, a Y-axis shift mechanism, and a Z-axis shift mechanism (wherein the terms "X-axis," "Y-axis," and "Z-axis" refer to the orthogonal axes in a Cartesian coordinate system. A body-holding component, configured to contact a body, can be attached to the frame such that the body-holding component extends from the frame to contact the body and hold the body relative to the frame. The frame is attached to the X-axis, Y-axis, and Z-axis shift mechanisms. The X-axis shift mechanism is configured to move the frame, with body-holding component, along an X-axis. The Y-axis shift mechanism is configured to move the frame, with body-holding component, along a Y-axis, wherein the movement along the Y-axis is independent of the movement along the X-axis. The Z-axis shift mechanism is configured to move the frame, with body-holding component, along a Z-axis, wherein the movement along the Z-axis is independent of the movement along the X-axis or along the Y-axis. The shift mechanisms are configured relative to each other so as to define a reference X-axis, a reference Y-axis, and a reference Z-axis, respectively, that are orthogonal relative to each other and that mutually intersect at a 0,0,0 point in three-dimensional space. The X-axis shift mechanism, Y-axis shift mechanism, and Z-axis shift mechanism are configured to move a body, mounted to the frame by the body-holding component, as required to place a selected point on or in the body at the 0,0,0 point.

The stereotaxic holder as summarized above can further comprise one or more of an X-axis tilting mechanism, a Y-axis tilting mechanism, and a Z-axis tilting mechanism. The X-axis tilting mechanism is configured to tilt a body, held by the frame, about the reference X-axis and relative to the 0,0,0 point. The Y-axis tilting mechanism is configured to tilt a body, held by the frame, about the reference Y-axis and relative to the 0,0,0 point. The Z-axis tilting mechanism is configured to tilt a body, held by the frame, about the reference Z-axis and relative to the 0,0,0 point. Each tilting motion is independent of any other tilting motion of the body or of any shifting motion of the frame as achieved by the stereotaxic holder.

The stereotaxic holder can further comprise at least one body-holding component attached to the frame. Exemplary body-holding components include, but are not limited to, ear bars and snout adapters.

In an example embodiment of a stereotaxic holder according to the invention, the frame is attached to the Z-axis shifting mechanism, the Z-axis shifting mechanism is attached to the X-axis shifting mechanism, and the X-axis shifting mechanism is attached to the Y-axis shifting mechanism. The example embodiment can further comprise a plate, wherein the X-axis tilting mechanism is attached to the plate. Hence, the Y-axis shifting mechanism is attached to the X-axis tilting mechanism, the Y-axis tilting mechanism is attached to the Y-axis shifting mechanism, the X-axis shifting mechanism is attached to the Y-axis tilting mechanism, and the Z-axis shifting mechanism is attached to the X-axis shifting mechanism. The plate can be mounted pivotably to a sub-plate to allow the plate to swing about the reference Z-axis. In such a configuration, the plate and sub-plate comprise the Z-axis tilting mechanism.

A second representative embodiment of a stereotaxic holder according to the invention comprises a first U-frame, a Z-axis shifting mechanism, an X-axis shifting mechanism, a Y-axis shifting mechanism, a Y-axis tilting mechanism, an X-axis tilting mechanism, and a Z-axis swing mechanism. A body-holding component, as summarized above, is attached to the first U-frame. The first U-frame is attached to the Z-axis shifting mechanism, which is configured to move the first U-frame, with body-holding component, along a Z-axis. The Z-axis shifting mechanism is attached to the X-axis shifting mechanism, which is configured to move the Z-axis shifting mechanism and first U-frame along an X-axis. The X-axis shifting mechanism is attached to the Y-axis shifting mechanism, which is configured to move the X-axis shifting mechanism, Z-axis shifting mechanism, and first U-frame along a Y-axis. The Y-axis tilting mechanism connects the X-axis shifting mechanism to the Y-axis shifting mechanism. The Y-axis tilting mechanism defines a reference Y-axis about which the Y-axis tilting mechanism effects tilting of the body. The Y-axis tilting mechanism is attached to the X-axis tilting mechanism, and the X-axis tilting mechanism is attached to the Z-axis swing mechanism. The X-axis tilting mechanism defines a reference X-axis about which the X-axis tilting mechanism effects tilting of the body, and the Z-axis swing mechanism defines a reference Z-axis about which the Z-axis swing mechanism effects a swing of the body. The reference X-axis, reference Y-axis, and reference Z-axis are orthogonal to each other and mutually intersect at a 0,0,0 point in three-dimensional space.

In the second representative embodiment as summarized above, the X-axis tilting mechanism can comprise a second U-frame having ends that pivot about the reference X-axis, and a base to which the Y-axis shifting mechanism is attached. In such a configuration, the Z-axis swing mechanism can comprise a plate and a sub-plate, wherein the X-axis tilting mechanism is attached to the plate and the plate is attached pivotably to the sub-plate to allow the plate to swing about the reference Z-axis.

According to another aspect of the invention, stereotaxic alignment systems are provided. A representative embodiment of such a system comprises a base plate and any of various stereotaxic holders according to the invention. For example, the stereotaxic holder can be configured as summarized above with respect to the first representative embodiment. In such a configuration, the stereotaxic holder can further comprise at least one of (desirably all three of) an X-axis tilting mechanism, a Y-axis tilting mechanism, and a Z-axis tilting mechanism. Each tilting mechanism, if present, is configured to tilt a body, held by the frame, about the respective reference axis and relative to the 0,0,0 point independently of any other tilting motion of the body or of any shifting motion of the frame.

In a stereotaxic alignment system according to the invention, the stereotaxic holder can include a centering gauge indicating the 0,0,0 point. For example, the centering gauge can be situated on the terminal face of a gauge post attached to the stereotaxic holder such that the gauge post is coaxial with the reference Z-axis.

Another representative embodiment of a stereotaxic alignment system according to the invention comprises a base plate, a stereotaxic holder (as summarized above) mounted to the base plate, and a manipulator mounted to the base plate. The manipulator includes a "controlled end" to which an implement can be mounted. Thus, the manipulator can present to the body a tool, held by the manipulator, at a desired locus on or in the body relative to the 0,0,0 point.

The manipulator desirably comprises an X-axis shifting mechanism, a Y-axis shifting mechanism, and a Z-axis shifting mechanism for shifting the controlled end along an X-axis, Y-axis, and Z-axis, respectively, relative to the 0,0,0 point. The manipulator further comprises a three-axis universal joint to which the X-axis shifting mechanism, the Y-axis shifting mechanism, and Z-axis shifting mechanism are mounted. The universal joint desirably is configured to allow adjustment of an orthogonal relationship of the X-axis, Y-axis, and Z-axis of the manipulator relative to each other. The universal joint can be configured further to allow adjustment of one or more of the X-axis, Y-axis, and Z-axis of the manipulator with one or more of the reference X-axis, reference Y-axis, and reference Z-axis of the stereotaxic holder.

In a stereotaxic alignment system according to the invention, the manipulator can include an implement mounted to the controlled end of the manipulator. Desirably, any of various implements has an alignment axis (usually the longitudinal axis of the implement). Desirably, any implement attachable to the controlled end is "self-indexing" as defined herein.

An exemplary implement is a centering scope usable with a centering gauge, as summarized above, that indicates the 0,0,0 point. The centering scope has an optical axis that is coincident with the alignment axis. In such an arrangement, the manipulator is configured to position the centering scope in an adjustable manner such that the optical axis intersects the centering gauge at the 0,0,0 point.

Other exemplary implements include, but are not limited to, drilling units, syringe holders, dial test indicators, cannula-insertion devices, and a stereotaxic alignment indicators.

According to another aspect of the invention, methods are provided for performing a stereotaxic alignment of a body. According to a representative embodiment of such a method, a reference X-axis, a reference Y-axis, and a reference Z-axis are provided that are orthogonal to each other and that mutually intersect at a 0,0,0 point in three-dimensional space. The body is mounted in a holder configured to effect respective controlled shifts of the body in an X-axis direction, a Y-axis direction, and a Z-axis direction, and to effect respective controlled tilts of the body about the reference X-axis and reference Y-axis, as well as controlled swings of the body about the reference Z-axis. Using the holder, the body is shifted as required in the X-axis, Y-axis, and Z-axis dimensions to place a selected target point on or in the body at the 0,0,0 point. Further using the holder, the body is subjected to a swinging motion as required about the reference Z-axis while maintaining the target point at the 0,0,0 point, to obtain a desired orientation of the body relative to the reference Y-axis or the reference X-axis. Further using the holder, the body is tilted as required about the reference Y-axis while maintaining the target point at the 0,0,0 point, so as to obtain a desired orientation of the body relative to the reference X-axis. Further using the holder, the body is tilted as required about the reference X-axis while maintaining the target point at the 0,0,0 point, so as to obtain a desired orientation of the body relative to the reference Y-axis. The step of swinging the body about the reference Z-axis can comprise the steps of: (1) identifying a first reference point and a second reference point on or in the body, wherein the first and second reference points define a reference line; and (2) swinging the body as required about the reference Z-axis until the reference line is at a desired orientation relative to the reference X-axis or the reference Y-axis. The reference line can be, for example, a sagittal axis of the body, wherein placing the reference line at the desired orientation achieves a sagittal alignment of the body.

The step of tilting the body about the reference Y-axis can comprise the steps of: (1) providing a stereotaxic alignment indicator for ascertaining the orientation of the body relative to the reference X-axis; (2) placing the stereotaxic alignment indicator into functional contact with the body; and (3) tilting the body as required until the stereotaxic alignment indicator indicates the desired orientation of the body about the reference Y-axis relative to the reference X-axis. For example, the body can be aligned to have its sagittal axis aligned with the reference Y-axis, wherein obtaining the desired orientation of the body about the reference Y-axis places the body at a desired coronal tilt.

The step of tilting the body about the reference X-axis can comprise the steps of: (1) providing a stereotaxic alignment indicator for ascertaining the orientation of the body relative to the reference Y-axis; (2) placing the stereotaxic alignment indicator into functional contact with the body; and (3) tilting the body as required until the stereotaxic alignment indicator indicates the desired orientation of the body about the reference X-axis relative to the reference Y-axis. For example, the body can be aligned to have its sagittal axis aligned with the reference Y-axis, wherein obtaining the desired orientation of the body about the reference X-axis places the body at a desired dorsal tilt.

The foregoing and additional features and advantages of the invention will be more apparent from the following detailed description, which proceeds with reference to the accompanying drawings.

DETAILED DESCRIPTION

To better understand the various motions of a body achievable using an apparatus according to the invention, the following information is useful. (When reviewing this information, it is helpful to envision a human body standing on its feet and facing straight ahead.) A median plane is a vertical plane that divides the body lengthwise into right and left halves. This plane is also termed a sagittal plane (because in a standing human it passes approximately through the sagittal suture in the skull), but actually any plane parallel to the medial plane is also termed a sagittal plane. A sagittal line or axis is a line on the sagittal plane extending lengthwise with respect to the subject's body (with a skull, such a line would extend roughly parallel to at least a portion of the sagittal suture). The coronal plane is a vertical plane that is perpendicular to the sagittal plane. (The coronal plane is so termed because in a standing human it passes approximately through the coronal suture in the skull.) Thus, the coronal plane divides the body into a front (ventral) half and a rear (dorsal) half. A coronal line or axis is a line in the coronal plane extending widthwise with respect to the subject's body (with a skull, such a line would extend roughly parallel to at least a portion of the coronal suture). A transverse plane is perpendicular to the sagittal and coronal planes. Ventral refers to the front (or belly surface) of the subject, and dorsal refers to the rear (or back surface) of the subject. Ventral and dorsal are synonymous with anterior and posterior, respectively.

A representative embodiment of a stereotaxic alignment system according to the invention comprises a stereotaxic holder 10 (such as the embodiment shown in FIGS. 1(a) and 1(b) and described below). For improved stability, the stereotaxic holder 10 desirably is mounted on a heavy base such as shown in FIG. 2.

Figure 1A:
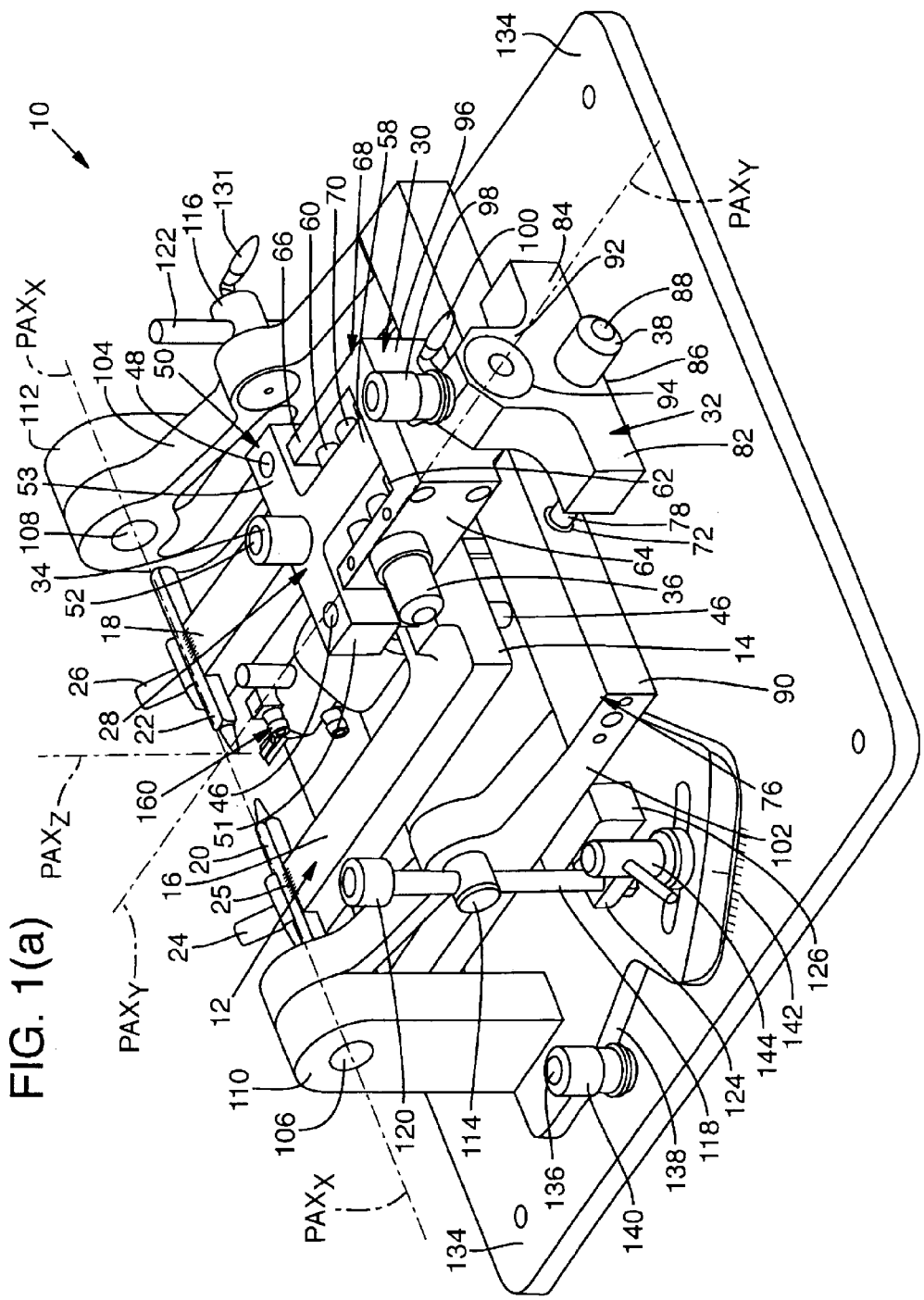
FIG. 1(a) is an oblique rear view of a representative stereotaxic holder, according to the invention, including a snout adapter and ear bars for holding a rodent skull.
Figure 1B:
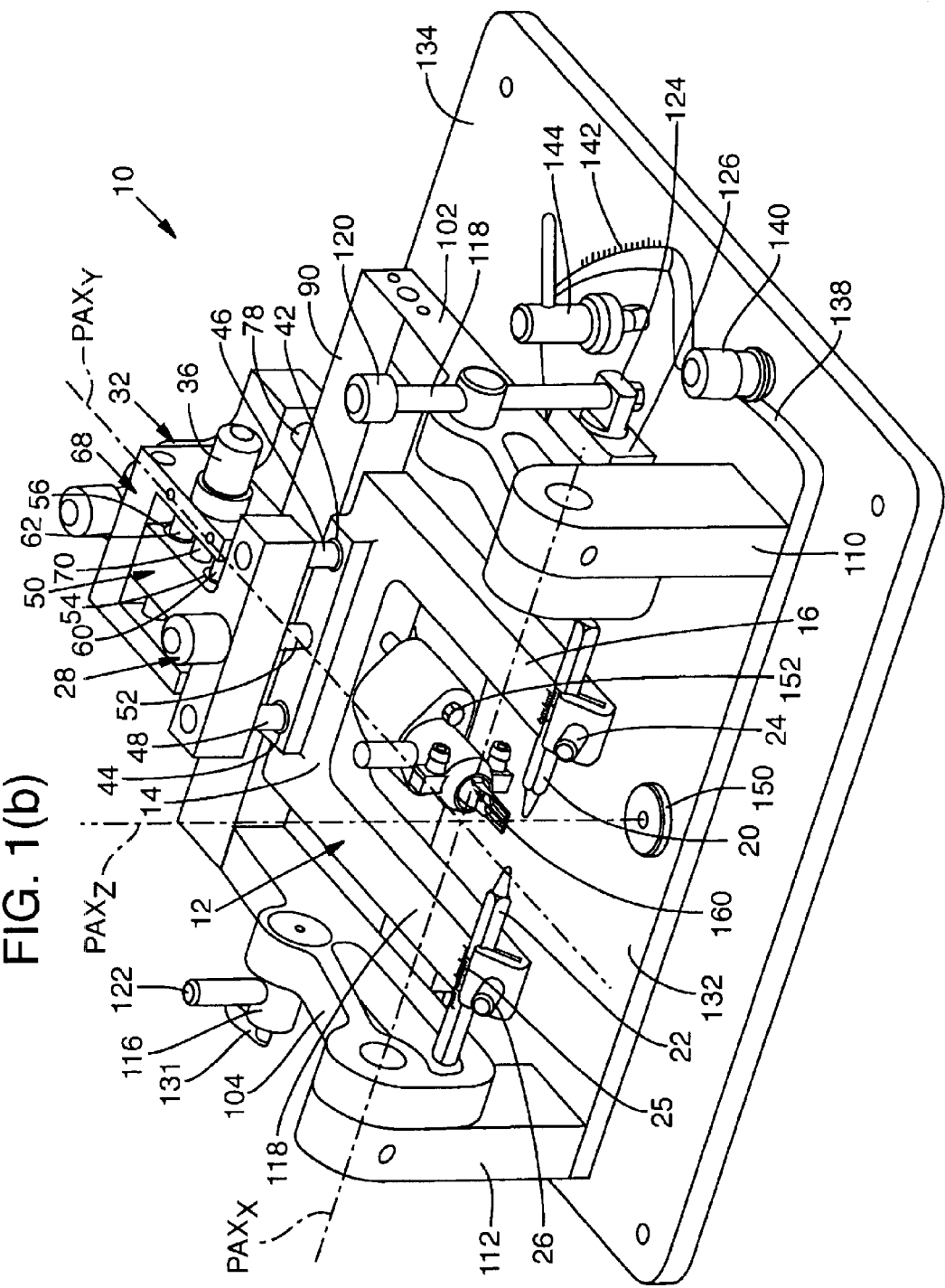
FIG. 1(b) is an oblique front view of the FIG. 1(a) embodiment, including a snout adapter and ear bars for holding a rodent skull.
Figure 2:
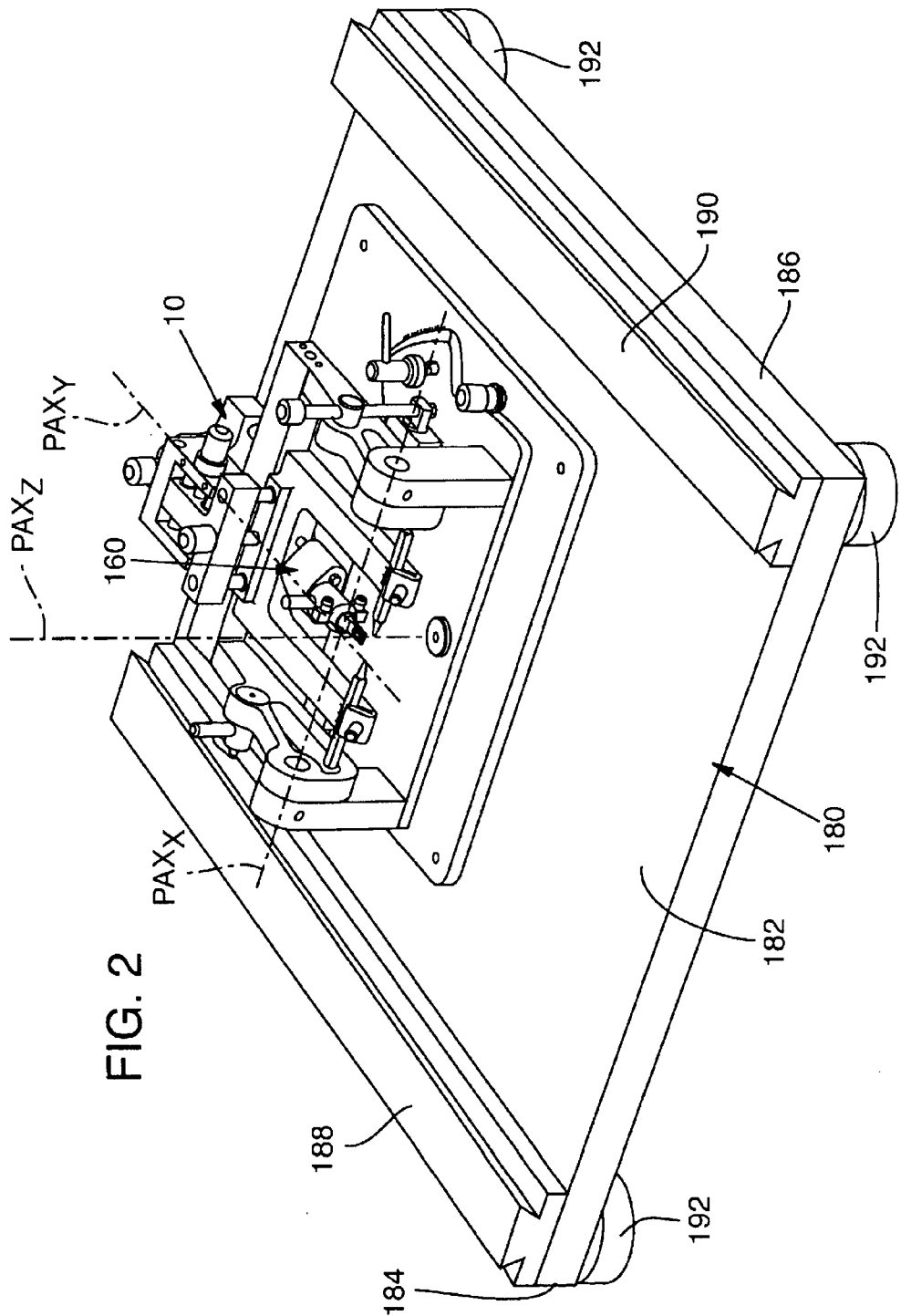
FIG. 2 is an oblique front view of the stereotaxic holder embodiment of FIG. 1(a) attached to a base.

The embodiment of FIGS. 1(a) and 1(b) is adapted especially for mounting and positioning of the head of a surgical or diagnostic subject (e.g., a rodent) in three-dimensional space to a reference position, and for rotating the subject's head into a desired three-dimensional position or stereotaxic plane. To such end, the stereotaxic holder comprises multiple slide mechanisms for controlled movement and placement of the subject's head in all three Cartesian dimensions. However, it readily will be appreciated that the relative dimensions of components of this embodiment can be changed to enable the apparatus to accommodate any size or configuration of body or body structure to be held by it.

A subject "body" (which can be a portion of an actual body) is held using components conveniently mounted to a first U-frame 12. The first U-frame 12 includes a center portion (base) 14 and first and second arms 16, 18, respectively. As discussed later, to the center portion 14 can be attached, for example, an appropriate snout adapter for holding the anterior end of a rodent skull. Each arm 16, 18 of the first U-frame 12 terminates with a respective ear bar 20, 22, respectively. The ear bars 20, 22 extend from the respective arms 16, 18 toward each other to engage the respective ear openings in the subject's skull. For ease of mounting the skull to the first U-frame 12, the spacing between the ear bars 20, 22 desirably is adjustable by loosening knurled screws 24, 26, sliding the ear bars 20, 22 toward or away from each other (a scale 25 on each ear bar 20, 22 can be used as a guide), and then tightening the knurled screws 24, 26.

It readily will be appreciated that the ear bars 20, 22 can be replaced with any of various other grasping, centering, or holding implements especially configured to engage a particular corresponding physical feature of a subject body to be held by the stereotaxic holder 10.

The first U-frame 12 is supported by an assembly of slide (or "shift") mechanisms that collectively allow positioning motions of the first U-frame 12 (and thus a skull or other body held by the first U-frame) linearly along the three Cartesian axes (X-, Y-, and Z-axis). Briefly, referring to FIG. 1(a), a Z-axis shift mechanism 28 provides shift motion of the first U-frame 12 along the indicated Z-axis; an X-axis shift mechanism 30 provides shift motion of the first U-frame 12 along the indicated X-axis; and a Y-axis shift mechanism 32 provides shift motion of the first U-frame 12 along the indicated Y-axis. Motion along the Z-axis is achieved by turning the knurled knob 34 that actuates the Z-axis shift mechanism 28. Motion along the X-axis is achieved by turning the knurled knob 36 that actuates the X-axis shift mechanism 30. Motion along the Y-axis is achieved by turning the knurled knob 38 that actuates the Y-axis shift mechanism 32.

Whereas, in the embodiment of FIGS. 1(a) and 1(b), the knurled knobs 34, 36, 38 are adapted especially for manual turning, it is contemplated that such turnings can be made using, by way of example, any of various wheels, cranks, levers, or motors. Also, whereas the depicted embodiment utilizes slide mechanisms each employing parallel guide bars and a lead screw, as described below, it readily will be apparent that any of various other linear displacement mechanisms can be employed, such as (but not limited to) dovetail slides and linear ball slides.

In more detail, the base 14 of the first U-frame 12 is attached to the Z-axis shift mechanism 28. The Z-axis shift mechanism 28 comprises two parallel bushings 42, 44 or linear bearings (generally termed "bushings") mounted in the base 14 of the first U-frame 12. Respective parallel guide bars 46, 48 are inserted into the bushings 42, 44 and extend to respective arms 51, 53 of a first T-member 50 to which the guide bars are affixed. A lead screw 52, attached to the knurled knob 34, extends through the first T-member 50, and is threaded into the base 14 of the first U-frame 12. Thus, turning the knurled knob 34 causes shift motion (along the Z-axis) of the first U-frame 12 along the guide bars 46, 48 relative to the first T-member 50.

Turning now to the X-axis shift mechanism 30, two parallel bushings 54, 56 or linear bearings (generally termed "bushings") are mounted in the stem 58 of the first T-member 50. Respective parallel guide bars 60, 62 are inserted into the bushings 54, 56 and extend to opposing arms 64, 66 of a second U-frame 68 to which the guide bars 60, 62 are affixed. A lead screw 70 is attached to the knurled knob 36, extends through one arm 64 of the second U-frame 68, is threaded into the stem 58 of the first T-member 50, and is journaled in the second arm 66 of the second U-frame 68. Thus, turning the knurled knob 36 causes shift motion (along the X-axis) of the first T-member 50 (with attached first U-frame 12) along the guide bars 60, 62 relative to the second U-frame 68.

Turning now to the Y-axis shift mechanism 32, two parallel bushings 72, 74 or linear bearings (generally termed "bushings") are mounted in the base 90 of a third U-frame 76. Respective parallel guide bars 78, 80 are inserted into the bushings 72, 74 and extend to respective arms 82, 84 of a second T-member 86 to which the guide bars 78, 80 are affixed. A lead screw 88 is attached to the knurled knob 38, extends through the second T-member 86, and is threaded into the base 90 of the third U-frame 76. Thus, turning the knurled knob 38 causes shift motion (along the Y-axis) of the X-axis shift mechanism 30, the Z-axis shift mechanism 32, and the first U-frame 12 along the guide bars 78, 80 relative to the third U-frame 76.

In addition to the X-, Y-, and Z-axis shift mechanisms 30, 32, 28, respectively, discussed above for achieving respective linear positioning motions along the three Cartesian axes, the embodiment of FIGS. 1(a) and 1(b) also is configured to effect pivoting ("tilt" and "swing") motions about each of three Cartesian reference axes.

The reference Y-axis about which Y-axis tilting motion can be achieved is denoted "$PAX_Y$" in FIGS. 1(a) and 1(b) and extends through the stem 92 of the second T-member 86. Specifically, a shaft 94 is attached to the base 96 of the second U-frame 68 and is journaled in the stem 92 of the second T-member 86. A knurled knob 98 is used to effect rotation of a gear (or analogous means) engaged with the shaft 94 or with the base 96; i.e., turning of the knurled knob 98 effects tilting of the second U-frame 68, Z-axis shift mechanism 28, and X-axis shift mechanism 30 (and all components attached thereto) about the axis $PAX_Y$. A particular angular position about the axis $PAX_Y$ can be "locked" by tightening a cinching screw 100.

The reference X-axis about which X-axis tilting motion can be achieved is denoted "$PAX_X$" in FIGS. 1(a) and 1(b). The axis $PAX_X$ extends through the termini of the arms 102, 104 of the third U-frame 76. Specifically, the arms 102, 104 are attached via respective shafts 106, 108 to respective blocks 110, 112 allowing tilting motion of the third U-frame 76 (including all components attached thereto) about the axis $PAX_X$. To achieve such tilting motion in a controllable manner, a respective block or other suitable member 114, 116 is attached rotatably to each arm 102, 104 of the third U-frame 76. (The figure shows such attachment at about the midline of each arm 102, 104, but such a configuration is not limiting in any way.) Threaded through one block 114 is a lead screw 118 terminating with a knurled knob 120, and extending through the other block 116 is a guide bar 122. The lead screw 118 is affixed rotatably to a respective member 124 that, in turn, is journaled in a respective block 126 or other suitable member. Similarly, the guide bar 122 is affixed to a respective member 128 that, in turn, is journaled in a respective block 130 or other suitable member. The blocks 126, 130 are affixed to a plate 132 to which the blocks 110, 112 are also attached. Thus, turning the knurled knob 120 effects tilting motion of the third U-frame 76 relative to the plate 132 about the axis $PAX_X$. After attaining a desired position of the third U-frame 76, a cinching screw 131 can be tightened onto the guide bar 122.

The reference Z-axis about which Z-axis pivoting motion ("swing") can be achieved is denoted "$PAX_Z$" in FIGS. 1(a) and 1(b). The axis $PAX_z$ extends through the plate 132 into a sub-plate 134. The plate 132 is attached rotatably to the sub-plate 134 in any suitable manner allowing motion of the plate 132 relative to the sub-plate 134 about the axis $PAX_Z$. Motion of this type in a controlled manner desirably is effected by turning a shaft 136 engaged (e.g., by a gear engagement or tire engagement) with a curved edge 138 of the plate 132. The shaft 136 is journaled in the sub-plate 134 and terminates with a knurled knob 140. Thus, turning the knurled knob 140 effects motion (swing) of the plate 132 about the axis $PAX_Z$ relative to the sub-plate 134. The angular orientation of the plate 132 relative to the sub-plate 134 can be ascertained by consulting a protractor scale 142. The desired angular orientation can be "locked" by tightening a cinching screw 144.

Figure 1C:
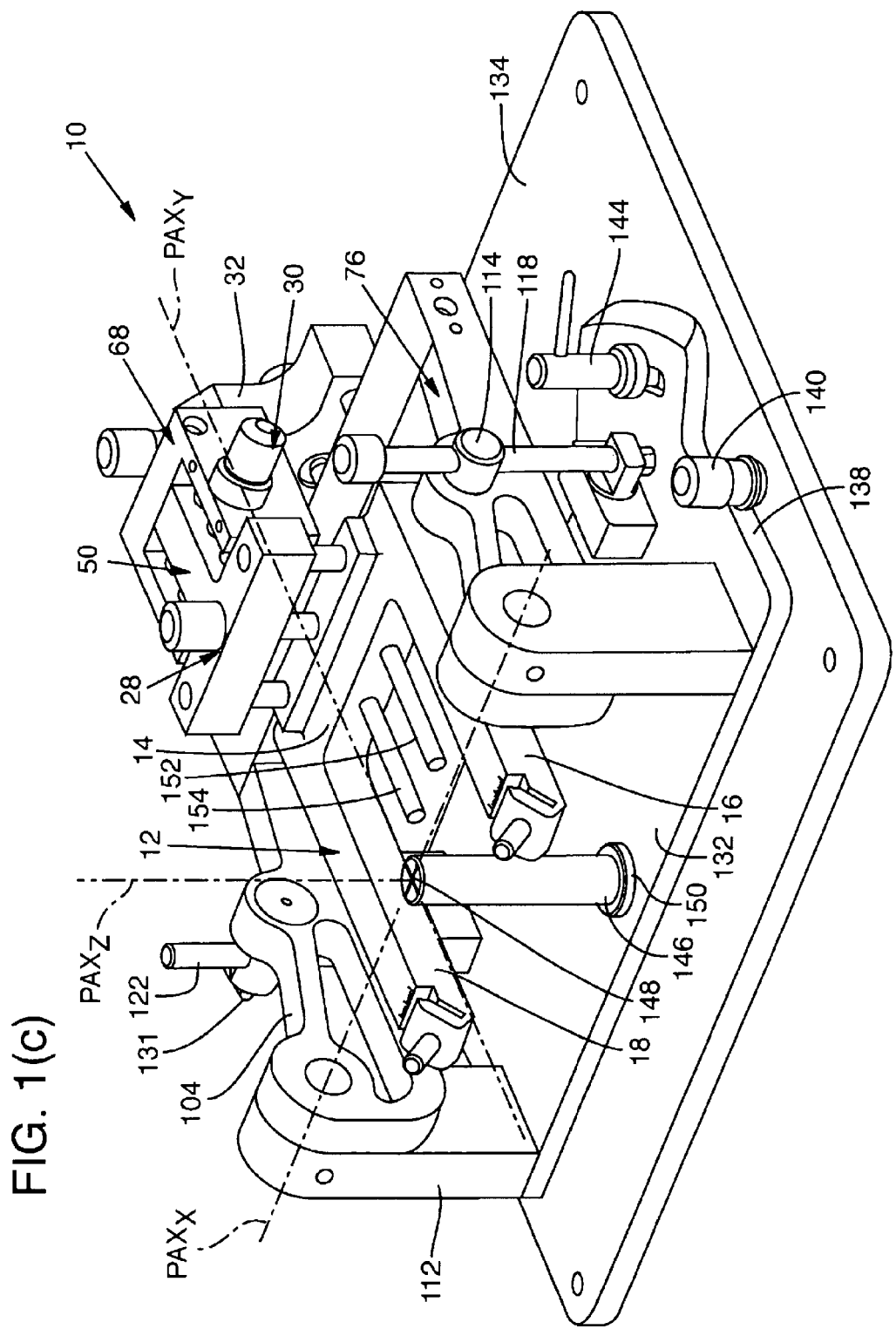
FIG. 1(c) is an oblique front view of the FIG. 1(a) embodiment, but with the snout adapter and ear bars removed and a gauge post attached.

FIG. 1(c) shows, extending upward along the axis $PAX_Z$, a removable gauge post 146 terminating with a "centering gauge" 148. The gauge post 146 has a fixed length relative to the plate 132 and is adapted to be mounted on a pad 150 on the plate 132. Whenever the gauge post 146 is so mounted, it is coaxial with the axis $PAX_Z$, and the axes $PAX_X$ and $PAX_Y$ pass through and intersect in the center of the centering gauge 148. The centering gauge 148 includes an appropriate cross-hair reticle or target that indicates the point of intersection of the three axes $PAX_X$, $PAX_Y$, and $PAX_Z$. During operation of the FIG. 1 embodiment, all axes of rotation for aligning the subject's skull (or other body held by the first U-frame 12) into the desired stereotaxic plane are focused at this mutual point of intersection. For example, if the FIG. 1 apparatus is used to hold a mouse head, then the point of intersection can be at bregma on the subject skull to establish a center of rotation, at bregma, for all three axes $PAX_X$, $PAX_Y$, $PAX_Z$. The ability of an apparatus according to the invention to establish this focal point of rotation for all three axes is in stark contrast to apparatus according to the prior art in which the focus of rotation is centered about, e.g., the intersection of "ear bar zero" and the medial plane. With a rodent skull, use of bregma as the center of rotation for all three axes is a key advantage in being able, using an apparatus according to the invention, to position a probe very accurately at a locus within the rodent brain that is situated, according to a brain atlas or other reference data, at a specified location relative to bregma or relative to bregma and lambda.

It will be appreciated readily that the principles of the present invention are not limited to centering on bregma. Rather, any natural or artificial reference point on or in a body can be used. For example, aside from any of various natural anatomical reference points, the reference point actually utilized can be an implanted bead of a substance readily visible using an X-ray, ultrasonic imager, or MRI imager. Furthermore, although the components of any of the various embodiments within the scope of the invention desirably are made of metal (e.g., aluminum alloy) for most applications, some or all the components can be made of any of various other suitable rigid materials. For example, the stereotaxic holder 10 can be made of a rigid polymer that enables the holder to be used with an MRI imager without the stereotaxic holder itself interfering with MRI imaging of the body being held by the stereotaxic holder.

Depending upon the orientation of the body mounted to the apparatus of FIGS. 1(a) and 1(b), the axis $PAX_Z$ can be regarded as a "sagittal-swing axis," wherein a swing about the axis $PAX_Z$ is made as required to achieve sagittal alignment of the subject body. In the case of a rodent skull, sagittal alignment can achieve alignment of the sagittal suture with (parallel to) anterior-posterior motions of a manipulator (described below) usable in conjunction with the embodiment of FIGS. 1(a) and 1(b), wherein bregma and lambda are used as reference points for the alignment. I.e., sagittal alignment under such conditions results in bregma and lambda defining a line extending perpendicularly to the axis $PAX_X$ passing through bregma. Under such conditions, the axis $PAX_X$ can be regarded as a "dorsal-tilt axis" for aligning (in the context of a rodent skull) the sagittal suture exactly perpendicularly (or at another pre-determined angular orientation) relative to vertical motions of the manipulator. In other words, nose-up or nose-down tilts are made as required to align lambda with bregma horizontally (with the axis of rotation, $PAX_X$, passing horizontally through bregma and being parallel with lateral motions of the manipulator). Finally, under such conditions, the axis $PAX_Y$ can be regarded as a "coronal-tilt axis" about which the subject skull can be tilted laterally. The coronal-tilt axis passes horizontally through bregma and lambda parallel to the anterior-posterior motions of the manipulator.

Referring again to the embodiment shown in FIG. 1(c), first and second mounting bars 152, 154 extend from the base 14 of the first U-frame 12. The mounting bars 152, 154 extend toward the gauge post 146 and can be used for mounting an appropriate snout adapter 160 (FIG. 1(b)) or other suitable holding implement for the particular body to be held by the stereotaxic holder 10. A representative snout adapter is described later below.

Referring now to FIG. 2, a representative embodiment of a base 180 comprises a base plate 182 having first and second opposing lateral edges 184, 186. Adjacent and coextensive with each lateral edge is a respective dovetail rail 188, 190 or alternative analogous slide mechanism allowing attachment and detachment of implements (such as a manipulator 200 as described below) as well as controlled movement of attached implement(s) in the directions in which the rails 188, 190 extend. Beneath each corner of the base plate is a respective non-slip, adjustable, leveling pad 192 used to keep the base 180 level on a working surface and to keep the base firmly in place on the working surface. The base 180 shown in FIG. 2 includes a stereotaxic holder 10, such as the embodiment shown in FIGS. 1(a)–1(c), mounted thereto.

Figure 3:
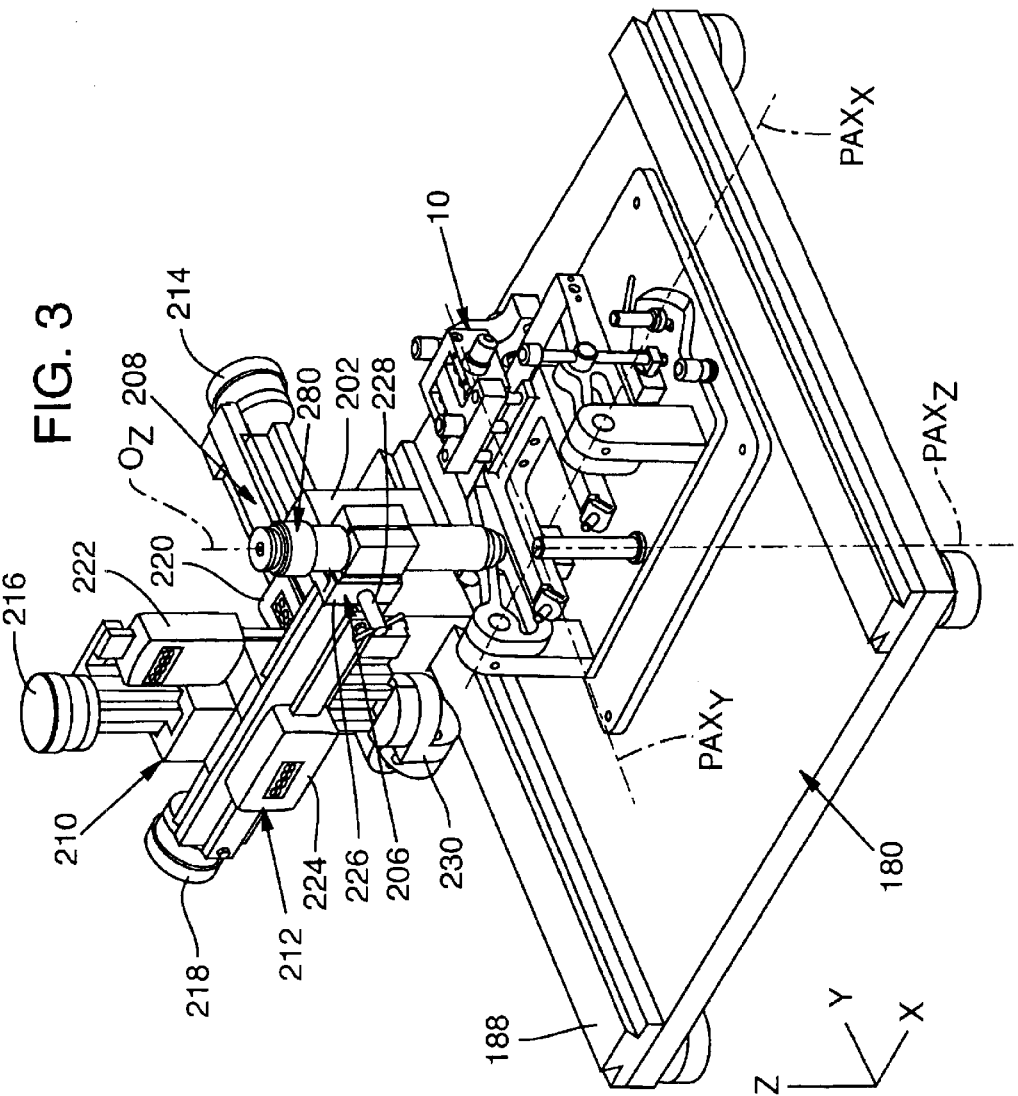
FIG. 3 is an oblique front view of a representative embodiment of a stereotaxic alignment system according to the invention, the system including the FIG. 2 embodiment including a manipulator attached to the base and a centering scope attached to the manipulator.
Figure 4:
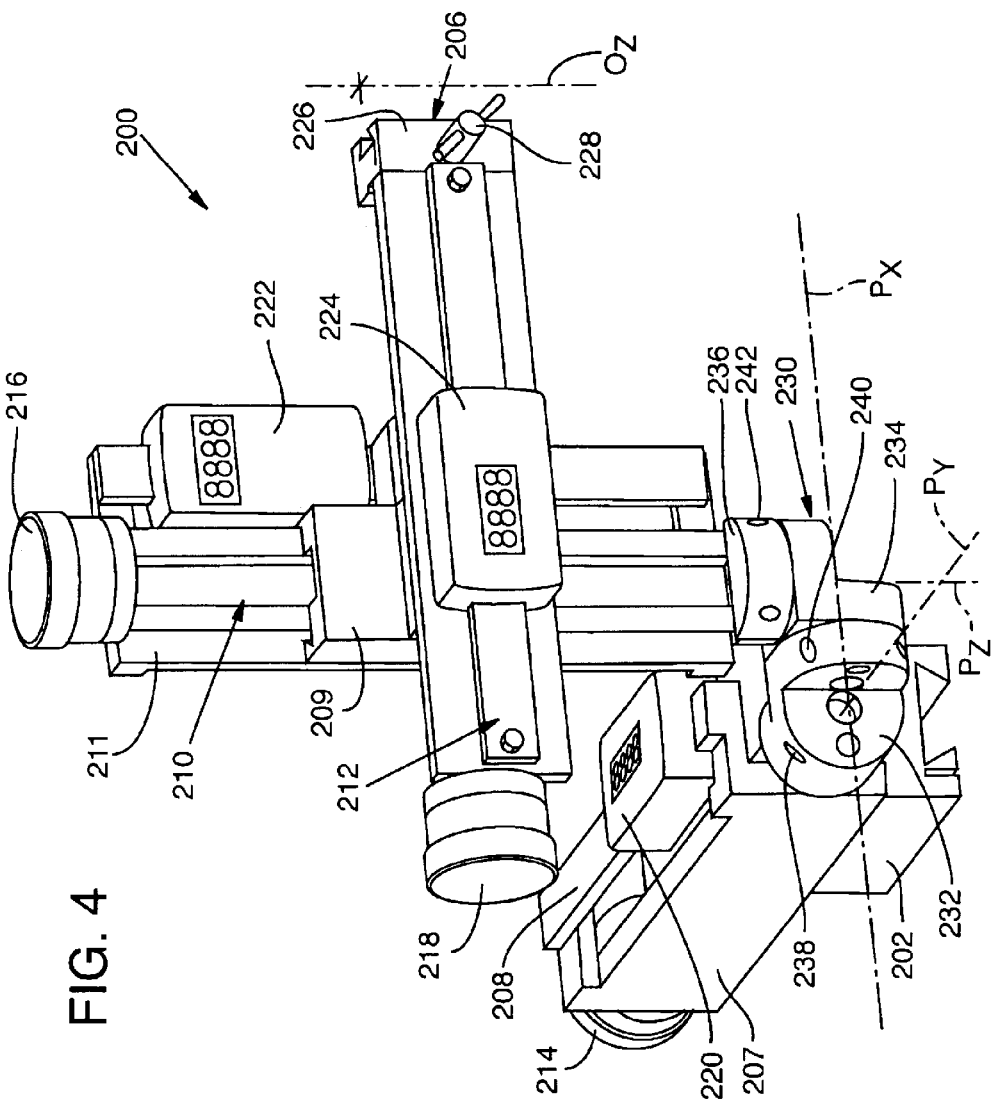
FIG. 4 is an enlarged oblique front view of a representative embodiment of a manipulator that can be included with a stereotaxic alignment system according to the invention. The FIG. 4 manipulator is substantially the same as shown in FIG. 3.

A representative embodiment of a manipulator 200 is shown in FIGS. 3 and 4. The depicted embodiment comprises a dovetail slide block 202 adapted to be mounted onto a dovetail rail 188, 190 (shown mounted on the dovetail rail 188) of the base 180, thereby permitting alignment of the Cartesian axes (X-, Y-, and Z-axes) of the manipulator 200 with the Cartesian axes $PAX_X$, $PAX_Y$, $PAX_Z$ of the stereotaxic holder 10. After mounting the manipulator 200 to the desired rail and sliding it to the desired location on the rail, the manipulator 200 can be affixed rigidly to the rail by tightening a cinching screw 204 (obstructed by foreground structure in this view) threaded into the slide block 202. The manipulator 200 comprises a distal "controlled end" 206 and a first shift mechanism 208, a second shift mechanism 210, and a third shift mechanism 212 for achieving controlled shift motions of the controlled end 206 along each of the three Cartesian axes (i.e., along the Y-axis, Z-axis, and X-axis, respectively). The first shift mechanism 208 is used for moving (after the manipulator 200 is mounted to the base 180) the controlled end 206 in the Y-direction in a controlled manner. To such end, the knurled knob 214 is turned, which causes a corresponding shift movement of a block 207 in the Y-direction relative to the block 202 (FIG. 4). The second shift mechanism 210 is used for moving the controlled end 206 in the Z-direction in a controlled manner. To such end, the knurled knob 216 is turned, which causes a corresponding shift movement of a block 209 relative to a guide member 211. Finally, the third shift mechanism 212 is used for moving the controlled end 206 in the X-direction in a controlled manner. To such end, the knurled knob 218 is turned, which causes a corresponding shift movement of a guide member 213 relative to the block 209. Each shift mechanism 208, 210, 212 is configured in the illustrated embodiment as a dovetail slide mechanism. However, as discussed above with respect to the stereotaxic holder 10, any of the shift mechanisms 208, 210, 212 alternatively can be any of various other analogous mechanisms. In the illustrated embodiment, each knurled knob 214, 216, 218 is attached to the terminus of a respective threaded shaft (not visible in the drawing).

In the embodiment depicted in FIGS. 3 and 4, each shift mechanism 208, 210, 212 includes a respective electronic digital scale 220, 222, 224 that displays a measured position along the respective axis. (In a representative alternative embodiment, respective vernier scales, rather than electronic digital scales, can be used to display shift position along each of the respective Cartesian axes.) Compared to a vernier scale, an electronic digital scale has advantages including greater resolution, lesser probability of reading errors, and capability of being reset to "zero" along the respective axis. Exemplary digital scales include DIGIMATIC™ scales (e.g., series 572) manufactured by Mitutoyo, Japan. Another candidate digital scale is any of various highly accurate "glass scales" such as DRO model 211 manufactured by Anilam, Miramar, Fla. By way of example only, with respect to a manipulator having shift movement ranges suitable for a mouse or rat animal subject, each of the shift mechanisms 208, 210, 212 has a motion range of 70 mm along the respective axis. It will be understood readily that these ranges can be made larger or smaller as required to accommodate larger or smaller subjects, respectively.

The controlled end 206 of the manipulator 200 is configured (by any of various possible attachment means) to have any of various implements attached to it. Thus, after performing alignment of the Cartesian axes of the manipulator 200 with the respective axes of the stereotaxic holder 10, an attached implement can be shifted along each of the Cartesian axes of the stereotaxic holder 10 in a controlled manner. By way of example, the depicted embodiment (FIG. 4) defines a female dovetail block 226. Each of the various implements that are attachable individually to a controlled end 206 having such a configuration has a conforming male dovetail rail segment mounted to an adapter block. The male dovetail rail segment allows the implement to slide into the female dovetail block 226 and thus be affixed to the controlled end 206. A cinching screw 228 is used to tighten the implement on the controlled end 206.

Desirably, for reasons that will be more apparent from the following discussion, the adapter block on each implement desirably is "self-indexing" with respect to the controlled end 206. By "self-indexing" is meant that any of various implements attachable to the controlled end can be attached with the functional end of the implement being at the same location, in three dimensional space, from one implement to the next. To such end, using the depicted embodiment by way of example, the female dovetail block 226 on the manipulator and/or the adapter block on each implement is provided with a mechanical stop (e.g., a pin or the like, not shown) that engages the other block in a consistent manner. Thus, the adapter block of any of various implements is mountable at exactly the same position, from one implement to another, relative to the female dovetail block 226. Self-indexing allows any of various implements to be attached to the manipulator without a need to re-adjust the manipulator or implement immediately after each mounting.

Many implements mountable to the controlled end 206 have a longitudinal axis $O_Z$. Another advantage of the "self-indexing" feature is that the axis $O_Z$ of any implement mounted on the controlled end 206 is, so long as the manipulator has not been adjusted in the meantime, automatically coincident with the axis $O_Z$ of the previous implement and/or the subsequent implement mounted to the controlled end 206. Again, this eliminates a need to re-adjust the manipulator 200 after changing the implement mounted to the controlled end 206.

The manipulator 200 desirably also includes a 3-axis universal joint 230. As shown in FIG. 4, the universal joint 230 comprises a first pivot block 232 mounted to an end of the block 207, a second pivot block 234 tiltably mounted to the first pivot block 232, and a third pivot block 236 swingably mounted to the second pivot block 234. An end of the guide member 211 is mounted to the third pivot block 236. The first pivot block 232 is tilted controllably as required about a first pivot axis $P_Y$ relative to the block 207 by turning a respective jack screw 238. The second pivot block 234 is tilted controllably about a second pivot axis $P_X$ relative to the first pivot block 232 by turning a respective jack screw 240. The third pivot block 236 is swung controllably as required about a third pivot axis $P_Z$ relative to the second pivot block 234 by turning a respective jack screw 242. Such controlled tilt and swing motions about one or more of the respective axes $P_X$, $P_Y$, and $P_Z$ are normally extremely limited in scope. They are performed normally whenever it is desired or necessary to bring the three Cartesian axes of shift motion of the controlled end 206 (achieved by the manipulator 200) into exact orthogonal relationship with each other and/or to align the three Cartesian axes of shift motion of the controlled end 206 (achieved by the manipulator 200) exactly with the three Cartesian axes of the stereotaxic holder 10. Such adjustments can be advantageous after the manipulator 200 and/or stereotaxic holder 10 are mounted to the base 180.

Figure 5:
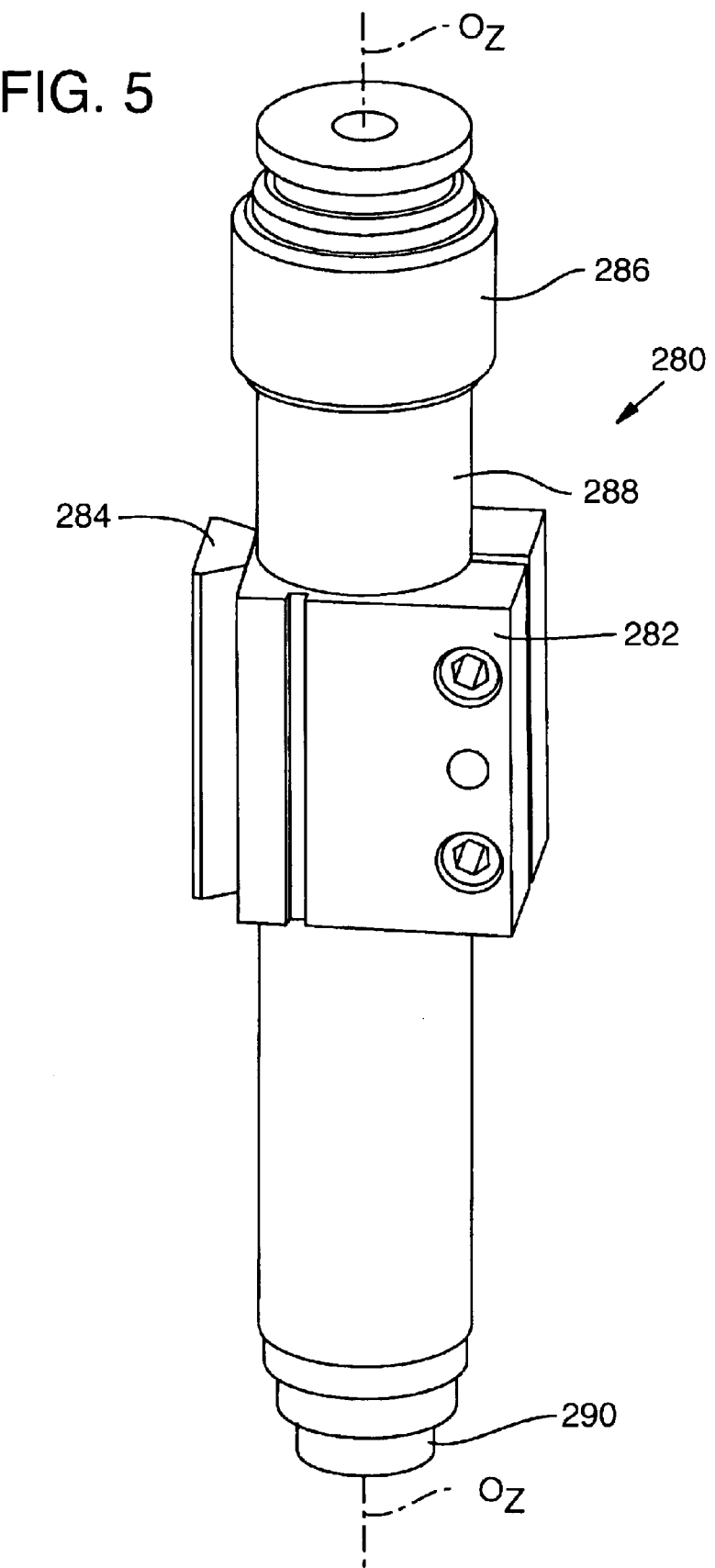
FIG. 5 shows details of a centering scope as a first representative implement that can be mounted to a manipulator of a stereotaxic alignment system according to the invention.

A first example implement mountable to the controlled end 206 is a centering scope 280, a representative embodiment of which is shown in FIG. 5. The centering scope 280, when attached to the controlled end 206 of the manipulator 200, desirably includes a cross-hair reticle or other suitable "optical finder" that can be trained on the reticle or cross-hair target of the centering gauge 148 and thus be used as an optical locating and centering device. The centering scope 280 includes a self-indexing adapter block 282 fitted with a male dovetail rail segment 284 configured to slide into and be held in the female dovetail socket 226 of the electrode manipulator 200. The centering scope 280 includes an eyepiece lens 286, an optical tube 288, and an objective lens 290. The centering scope 280 can have any convenient magnification, such as 20x magnification, sufficient to obtain, for example, accurate alignment of the optical axis $O_Z$ of the centering scope with the axis $PAX_Z$ of the stereotaxic holder 10 (such alignment is shown in FIG. 4). After performing the alignment, the centering scope 280 can be detached from the controlled end 206 and a new implement attached to the controlled end with the longitudinal axis $O_Z$ of the implement automatically being aligned accurately with the axis $PAX_Z$. Further detail on use of the centering scope 280 is provided later.

Figure 6:
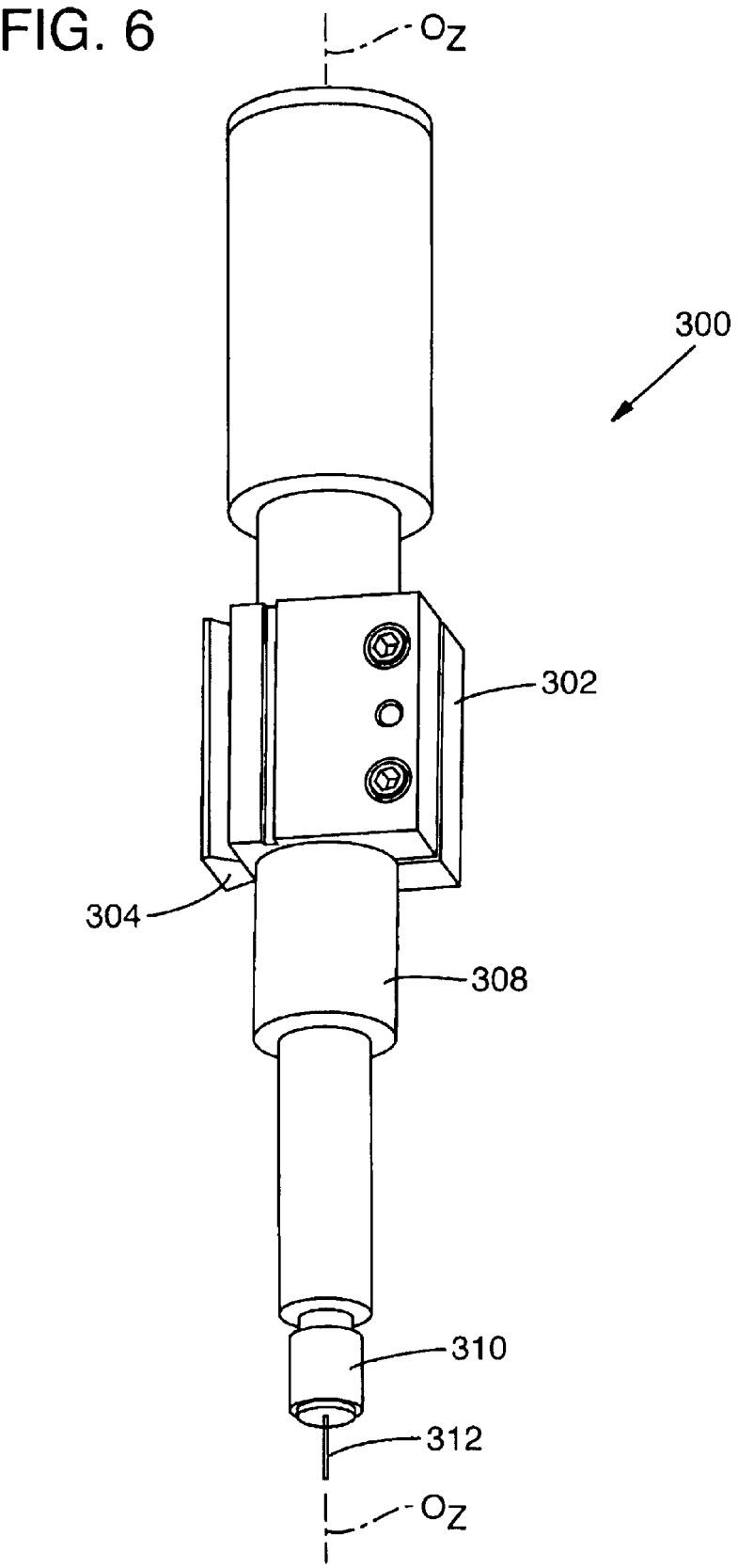
FIG. 6 shows details of a drilling unit as a second representative implement that can be mounted to a manipulator of a stereotaxic alignment system according to the invention.

A second example implement is a drilling unit 300 for use in drilling a hole in a subject animal's skull or for performing analogous tasks in preparation for implanting a probe at the desired locus in the subject body, or for any of various other surgical purposes. A representative embodiment of a drilling unit 300 is shown in FIG. 6, and includes a self-indexing adapter block 302, a male dovetail rail segment 304, motor 306, housing 308, and chuck 310 adapted to hold, e.g., a drill bit 312. Normally, the drilling unit 300, when mounted to the controlled end 206 of the electrode manipulator 200, presents the drill bit 312 coaxially with the axis $O_Z$ of the implement (e.g., the centering scope 280) previously attached to the controlled end.

Figure 7:
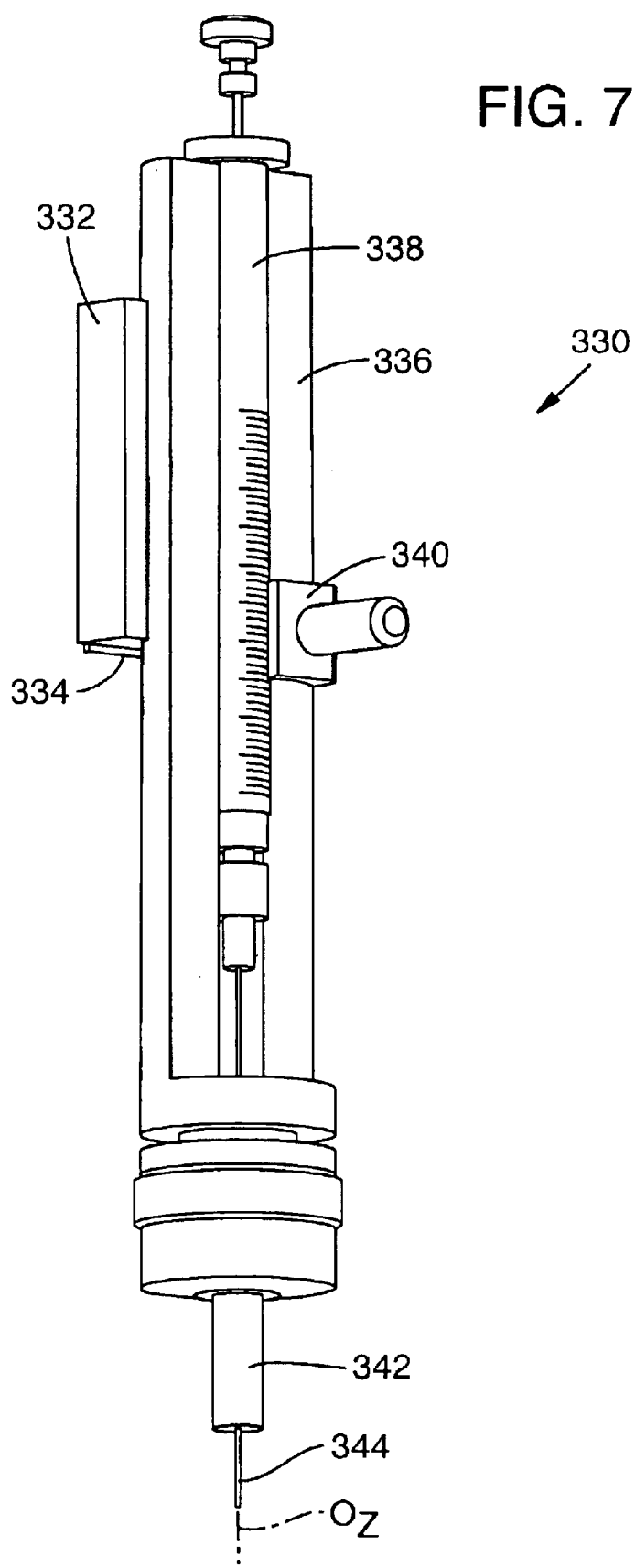
FIG. 7 shows details of a syringe holder as a third representative implement that can be mounted to a manipulator of a stereotaxic alignment system according to the invention.

A third example implement is a syringe holder 330 adapted to hold a surgical or microinjection syringe. A representative embodiment of a syringe holder 330 is shown in FIG. 7, and includes a self-indexing adapter block 332, a male dovetail rail segment 334, a syringe enclosure 336 configured and dimensioned to hold a particular type of syringe 338, an adjustable "zeroing" scale 340, and a needle guide tube 342. Normally, the syringe holder 330 presents a hollow needle 344 or probe to be inserted, along the axis $O_Z$, into the desired locus in the subject animal.

Figure 8:
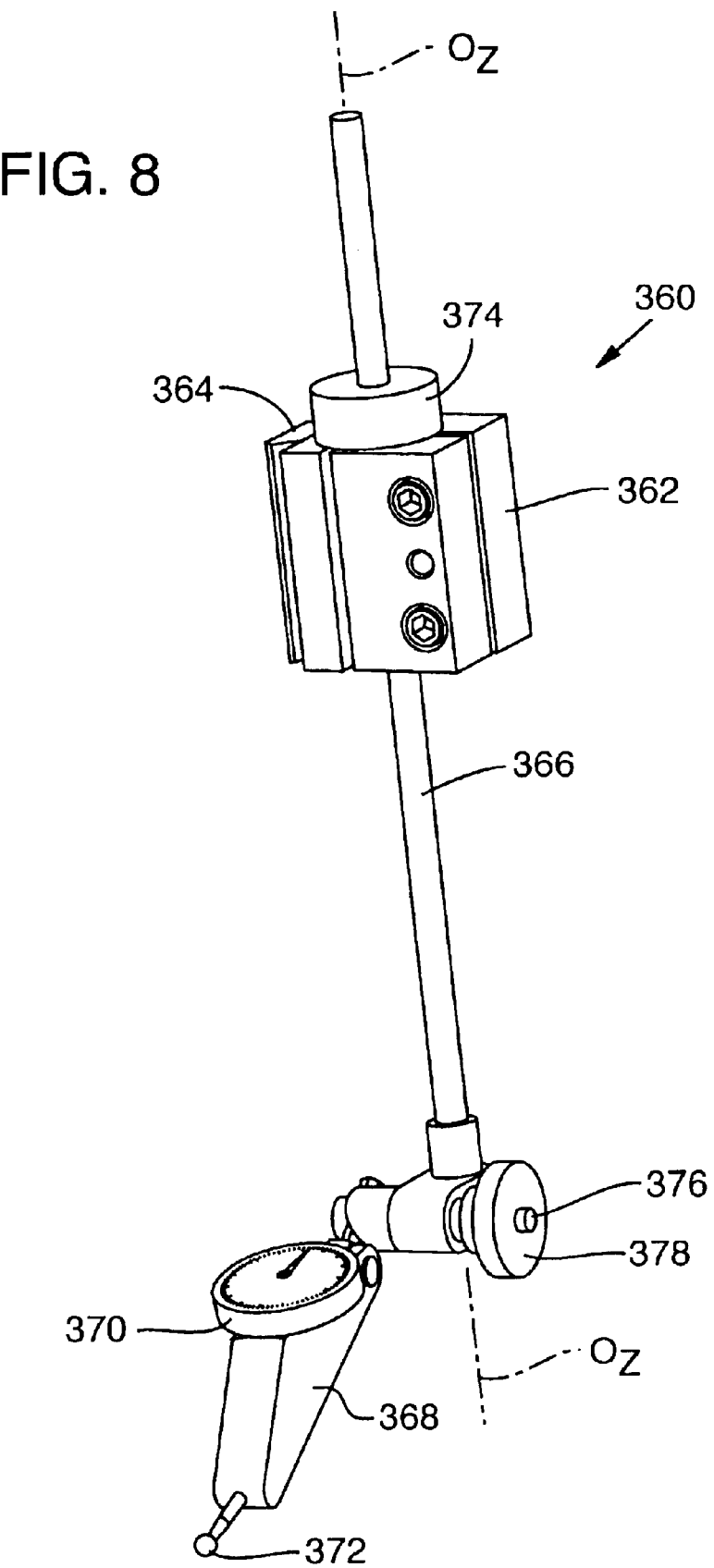
FIG. 8 shows details of a dial test indicator as a fourth representative implement that can be mounted to a manipulator of a stereotaxic alignment system according to the invention.

A fourth example implement is a dial test indicator unit 360 used for determining and calibrating the alignment of the axis $O_Z$, such as whether the axis $O_Z$ is oriented exactly perpendicularly to the surface of the plate 132 (or of the plate 182) and whether all three axes of the electrode manipulator 200 are exactly perpendicular to each other and/or exactly aligned with the corresponding Cartesian axes of the stereotaxic holder 10. Such determinations and calibrations are similar to analogous determinations and calibrations, respectively, (termed "sweeping in" or "indicating") performed with three-axis machine tools. A representative embodiment of a dial test indicator unit 360 is shown in FIG. 8, and includes a self-indexing adapter block 362, a male dovetail rail segment 364, a shaft 366 having an axis $O_Z$ alignable with or relative to the axis $PAX_Z$ of the stereotaxic holder 10, an arm 368 that is oriented angularly relative to the axis $O_Z$ in an adjustable manner, and a dial indicator 370 (e.g., LAST WORD™ indicator, model 711-MF, manufactured by Starrett, Athol, Mass.) including a contact point 372. The shaft 366 is rotatable relative to the adapter block 362, and can be manipulated to move (raise and lower) the position of the arm 368 (with dial indicator 370) along the axis $O_Z$. A collar 374 can be cinched onto the shaft 366 to hold the shaft 366 at a particular position along the axis $O_Z$ relative to the adapter block 362. A threaded shaft 376 (to which a knurled nut 374 is threaded) cinches the arm 368 at a desired angular orientation relative to the shaft 366.

As an example protocol with which the dial indicator can be used, the dial indicator is mounted to the controlled end 206 with the shaft 366 oriented vertically downward toward the surface of the plate 182. The contact point 372 is placed in contact with the surface of the plate 182. The user observes the numerical reading on the dial indicator 370 while rotating the shaft 366 about the axis $O_Z$. If the displayed numerical value changes with angle of rotation of the shaft 366, axial adjustment can be performed by turning the jack screws 238, 240 (FIG. 4) as required until the dial indicator 370 reads the same value with any angle of rotation.

Figure 9:
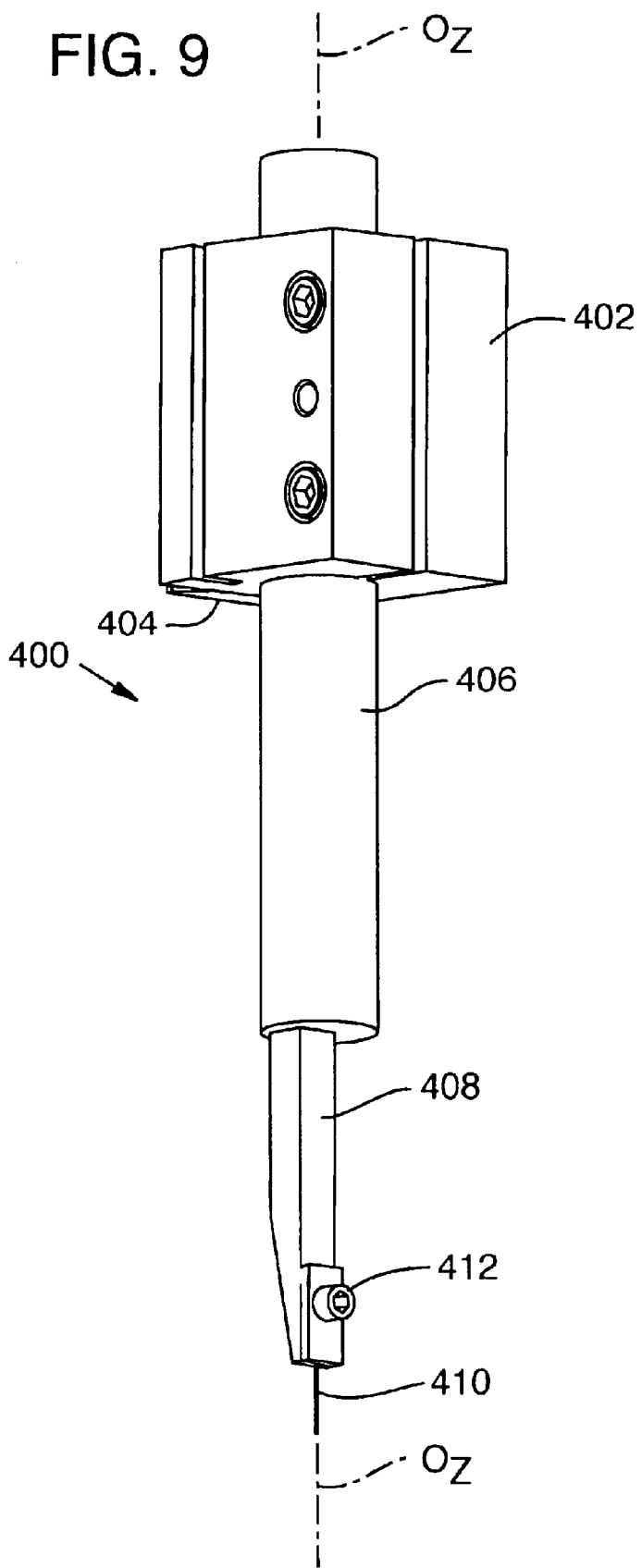
FIG. 9 shows details of a first representative embodiment of a cannula-insertion device as yet another example implement that can be mounted to a manipulator of a stereotaxic alignment system according to the invention.

A fifth example implement is any of various cannula-insertion devices. A first embodiment 400 of a cannula-insertion device is shown in FIG. 9. The FIG. 9 embodiment 400 is relatively simple and comprises a self-indexing adapter block 402, a male dovetail rail segment 404, a shaft 406 having an axis $O_Z$ alignable with or relative to the axis $PAX_Z$ of the stereotaxic holder 10, and a cannula-holding arm 408 configured to hold a cannula 410 (or analogous tool) such that a longitudinal axis thereof is aligned with the axis $O_Z$. A cinching screw 412 affixes the cannula 410 to the terminus of the arm 408. The FIG. 9 embodiment 400 can be used to hold and implant one cannula tube (or analogous tool) to a desired on-plane locus.

Figure 10:
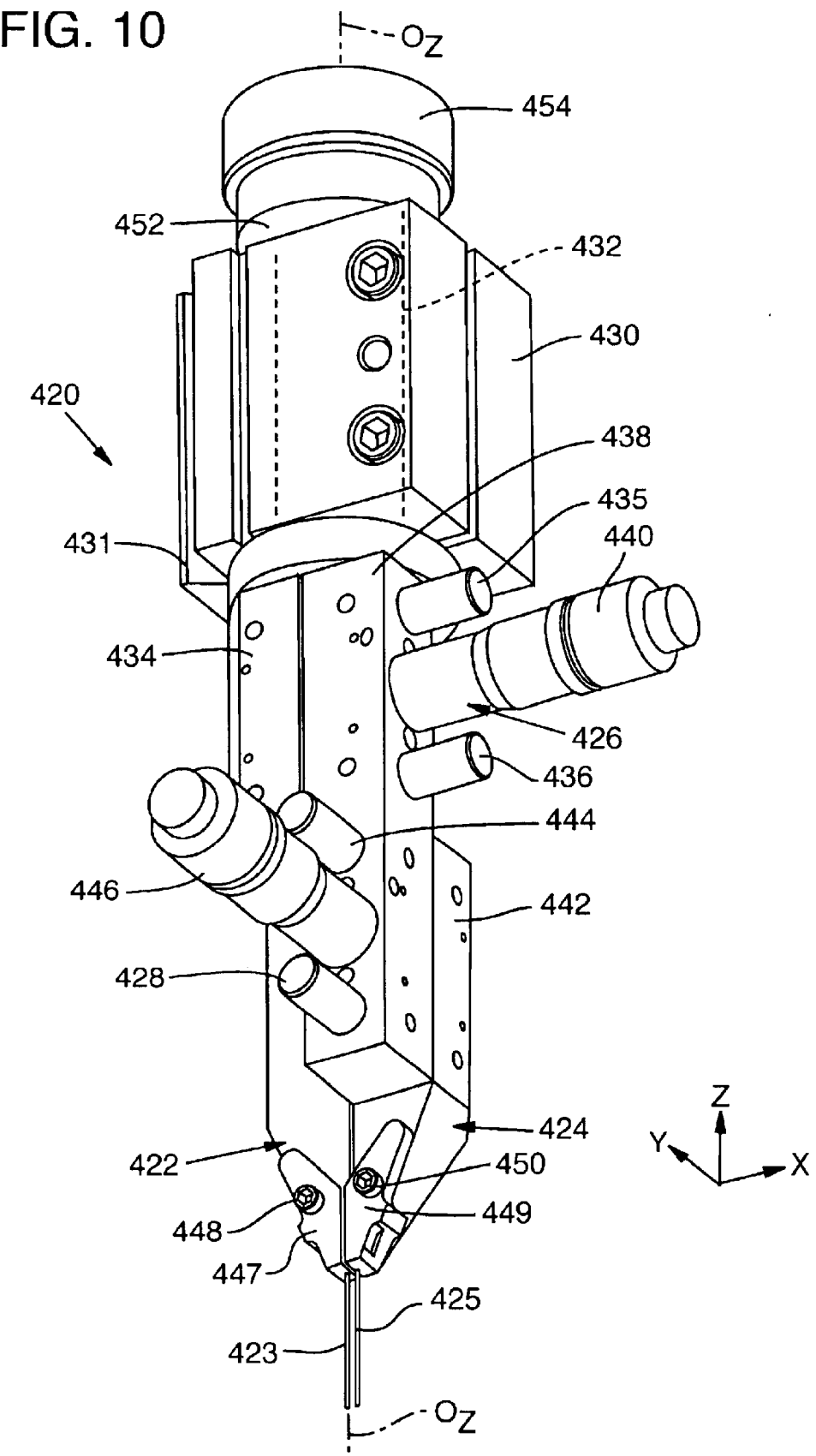
FIG. 10 shows details of a second representative embodiment of a cannula-insertion device as yet another example implement that can be mounted to a manipulator of a stereotaxic alignment system according to the invention.

A second embodiment 420 of a cannula-insertion device is shown in FIG. 10. The FIG. 10 embodiment 420 is especially suitable for holding and implanting one or two cannulae (or analogous tools) to respective on-plane loci. The FIG. 10 device comprises a first cannula holder 422 for holding a first cannula 423 (or other tool shaped similarly to a cannula) and a second cannula holder 424 for holding a second cannula 425 (or other tool shaped similarly to a cannula). Mounted in their respective holders 422, 424, each cannula 423, 425 can be placed at different respective X-axis and Y-axis coordinates. More specifically, the first cannula 423 held in the first cannula holder 422 is aligned longitudinally with the axis $O_Z$ (and thus directly alignable with or relative to the $PAX_Z$ axis of the stereotaxic holder 10). The second cannula 425 held in the second cannula holder 424 can be positioned relative to the first cannula 423 (while remaining parallel to the first cannula 423) by manipulating one or both of a first shift mechanism 426 and a second shift mechanism 428 described in more detail below.

The cannula-insertion device 420 comprises a self-indexing adapter block 430 including a male dovetail rail segment 431, a shaft 432 inserted into the adapter block 430 and having an axis $O_Z$, the first and second cannula holders 422, 424, respectively, and the first and second shift mechanisms 426, 428, respectively. The first shift mechanism 426 comprises a first member 434 attached to the shaft 432, first and second parallel guide bars 435, 436, respectively, affixed to the first member 434, and a second member 438 adapted to slide along the guide bars 435, 436. One or more extension springs (not shown) desirably are situated between the first and second members 434, 438 to urge the members to move together. A force counter to the spring force is applied by a first micrometer head 440 which, when turned, controllably adjusts the spacing (along the indicated X-axis) between the first and second members 434, 438, and thus the spacing (along the indicated X-axis) between the first and second cannulae 423, 425. The second shift mechanism 428 comprises a member 442 to which first and second guide bars 444, 445, respectively, are affixed. The guide bars 444, 445 slide relative to the member 438. One or more extension springs (not shown) desirably are situated between the members 438, 442 to urge the members to move together. A force counter to the spring force is applied by a second micrometer head 446 which, when turned, controllably adjusts the spacing (along the indicated Y-axis) between the members 438, 442 and thus the spacing (along the indicated Y-axis) between the first and second cannulae 423, 425. The member 434 terminates with a clamp 447 adapted to grip the first cannula 423 whenever the screw 448 is tightened. Similarly, the member 424 terminates with a clamp 449 adapted to grip the second cannula 425 whenever the screw 450 is tightened. On the opposite side of the adapter block 430 is a collar 452 attached to the adapter block 430 and coaxial with the axis $O_Z$. The shaft 432 terminates with a knurled knob 454 that, when turned, rotates the entire cannula-insertion device relative to the adapter block 430 about the axis $O_Z$ (i.e., about the indicated Z-axis). The angular orientation of the cannula-insertion device about the axis $O_Z$ can be locked by tightening a cinching screw (not shown) threaded through the collar 452 to engage the shaft 432.

Figure 11:
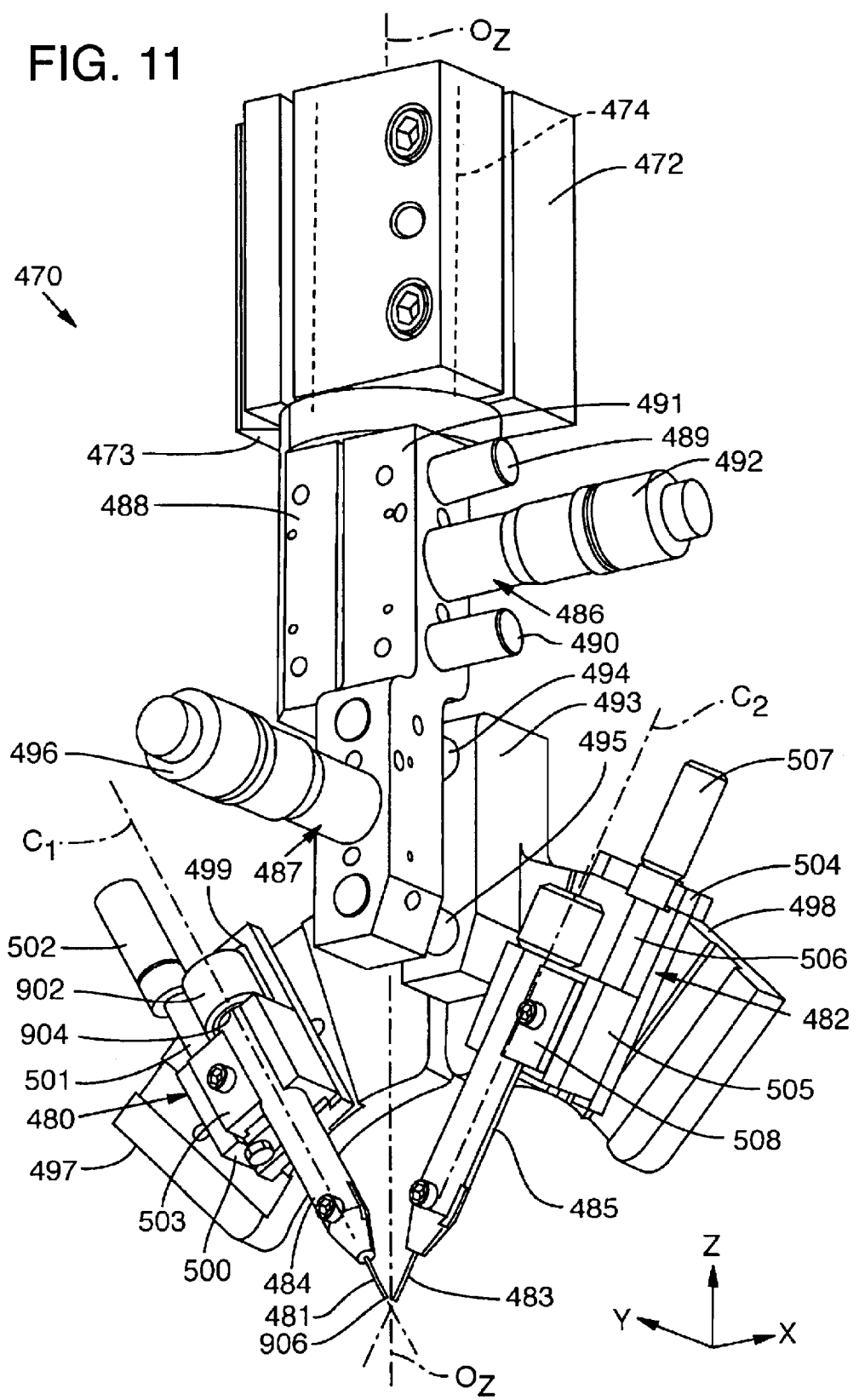
FIG. 11 shows details of a third representative embodiment of a cannula-insertion device as yet another example implement that can be mounted to a manipulator of a stereotaxic alignment system according to the invention.

A third embodiment 470 of a cannula-insertion device is shown in FIG. 11, which has especial utility for independently holding and implanting one or two cannulae to respective off-plane loci. The FIG. 11 device 470 comprises the following components that are similar to corresponding components (described above) in the FIG. 10 embodiment 420: self-indexing adapter block 472, male dovetail rail segment 473, and shaft 474. The FIG. 11 device 470 comprises a first cannula holder 480 for holding a first cannula 481 (or other tool shaped similarly to a cannula) and a second cannula holder 482 for holding a second cannula 483 (or other tool shaped similarly to a cannula). The first and second cannulae 481, 483, respectively, are held in first and second cannula adapters 484, 485, respectively, mounted to respective first and second cannula holders 480, 482, respectively. When so mounted, the terminus of the first cannula 481 and the terminus of the second cannula 483 can be placed at different respective X-axis and Y-axis coordinates by manipulating one or both of a first shift mechanism 486 and a second shift mechanism 487. Further detail regarding mounting the cannulae 481, 483 in the respective cannula adapters 484, 485, and mounting the cannula adapters 484, 485 in the respective cannula holders 480, 482 is provided later below.

The first shift mechanism 486, similar to the first shift mechanism 426 of the FIG. 10 embodiment 420, comprises a first member 488 attached to the shaft 474, first and second parallel guide bars 489, 490, respectively, affixed to the first member 488, and a second member 491 adapted to slide along the guide bars 489, 490. One or more extension springs (not shown) desirably are situated between the first and second members 488, 491 to urge the members to move together. A force counter to the spring force is applied by a first micrometer head 492 that, when turned, controllably adjusts the spacing (along the indicated X-axis) between the first and second members 488, 491, and thus the spacing (along the indicated X-axis) between the terminus of the first cannula 481 and the terminus of the second cannula 483. The second shift mechanism 487 comprises a member 493 to which first and second guide bars 494, 495, respectively, are affixed. The guide bars 494, 495 slide relative to the member 491. One or more extension springs (not shown) desirably are situated between the members 491, 493 to urge the members to move together. A force counter to the spring force is applied by a second micrometer head 496 that, when turned, controllably adjusts the spacing (along the indicated Y-axis) between the members 491, 493 and thus the spacing (along the indicated Y-axis) between the terminus of the first cannula 481 and the terminus of the second cannula 483.

To the member 488 is affixed a first arc plate 497, and to the member 493 is affixed a second arc plate 498. The first cannula holder 480 is attached to the first arc plate 497, and the second cannula holder 482 is attached to the second cannula holder 482. The first cannula holder 480 comprises a slide mechanism comprising a plate 499, a block 500 adapted to slide relative to the plate 499 as controlled by a lead screw 501 (manually turned using a knurled knob 502), and a tool clip 503 configured to grip the first cannula adapter 484 (or other suitably shaped tool). Thus, turning the knurled knob 502 controllably shifts the cannula 481 (or other tool) along a first cannula axis $C_1$. The plate 499 can be adjustably moved along the arc defined by the first arc plate 497 so as to change the angle of the first cannula axis $C_1$ relative to the axis $O_z$ (or to a line parallel to $O_z$). Similarly, the second cannula holder 482 comprises a slide mechanism comprising a plate 504, a block 505 adapted to slide relative to the plate 504 as controlled by a lead screw 506 (manually turned using a knurled knob 507), and a tool clip 508 configured to grip the second cannula adapter 485. Thus, turning the knurled knob 507 controllably shifts the cannula 483 along a second cannula axis $C_2$. The plate 504 can be moved adjustably along the arc defined by the second arc plate 498 so as to change the angle of the second cannula axis $C_2$ relative to the axis $O_z$. Furthermore, the respective angles of the cannula axes $C_1$, $C_2$ relative to $O_z$ (or to respective lines parallel to $O_z$) need not be the same and can be adjusted independently.

Figure 12:
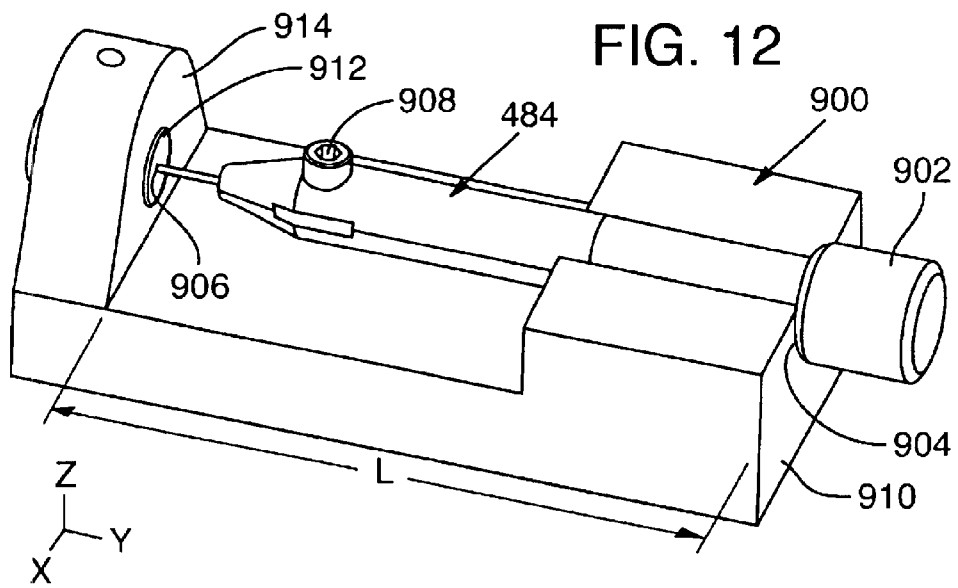
FIG. 12 depicts a cannula adapter, for use in the FIG. 11 embodiment of a cannula-insertion device, placed in a gauge block 900 used for facilitating auto-indexing of a cannula or other tool held by the cannula adapter when mounted to the cannula-insertion device.

Whenever the slide mechanism of the first cannula holder 480 is shifted fully downward, the first cannula 481 or other tool (held in the first cannula adapter 484 mounted to the first cannula holder 480) desirably is situated such that the terminus of the first cannula 481 (or other tool) is situated exactly on the axis $O_z$ (and thus directly alignable with the $PAX_z$ axis of the stereotaxic holder 10). To such end, the tool clip 503 and block 500, functioning in combination with the first cannula adapter 484, desirably are "self-indexing," as follows. FIG. 12 shows a first cannula adapter 484 (detached from the first cannula holder 480) placed in a "gauge block" 900. The first cannula adapter 484 includes a shoulder portion 902 having a facing surface 904. The gauge block 900 is used to establish a standard length (L) from the facing surface 904 to the terminus 906 of the cannula 481. The first cannula adapter 484 (with cannula 481 or other tool attached but with the screw 908 loosened) is placed in the gauge block 900 such that the facing surface 904 contacts a first surface 910 of the cannula adapter. Meanwhile, the terminus 906 of the cannula 481 is placed in contact with a hardened region 912 of a second surface 914. Afterward, the screw 908 is tightened to fasten the cannula 481 to the cannula adapter 484. The cannula adapter with attached cannula can be removed from the gauge block 900 and mounted to the first cannula holder 480 (FIG. 11) such that the facing surface 904 contacts the upward-facing surfaces of the tool clip 503 and the block 500. Whenever the cannula adapter 484 is mounted in such a manner to the first cannula holder 480 (with the slide mechanism of the first cannula holder 480 fully shifted downward), the terminus 906 of the first cannula 481 (or other tool) is situated exactly on the axis $O_z$ (as shown in FIG. 11), and thus directly alignable with or relative to the $PAX_z$ axis of the stereotaxic holder 10. Any other tool mounted to the first cannula adapter 484 in the manner described above will also have its terminus contact the axis $O_z$.

Desirably, the second cannula adapter 485 is "self-indexing" with respect to the second cannula holder 482 in the same manner as discussed above. It also will be appreciated that a cannula 483 or other tool can be mounted to the second cannula adapter 485, and the second cannula adapter mounted to the second cannula holder 482, in the same manner as described above regarding the first cannula. In any event, the terminus of the second cannula 483 (held in the second cannula adapter 485 mounted to the second cannula holder 482) can be positioned relative to the terminus of the first cannula 481 by manipulating one or both of the first shift mechanism 486 and the second shift mechanism 487.

Whenever the first cannula 481 has been mounted in a self-indexing manner as described above, so as to place the terminus of the first cannula on the axis $O_z$, the plate 499 can be moved adjustably along the arc defined by the first arc plate 497 so as to change the angle of the first cannula axis $C_1$ relative to the axis $O_z$ (or to a line parallel to $O_z$) without changing the location, in three-dimensional space, of the terminus of the first cannula 481. Similarly, whenever the second cannula 483 has been mounted in a self-indexing manner as described above, the plate 504 can be moved adjustably along the arc defined by the second arc plate 498 so as to change the angle of the second cannula axis $C_2$ relative to the axis $O_z$ (or to a line parallel to the axis $O_z$) without changing the location, in three-dimensional space, of the terminus of the second cannula 483.

As with the FIG. 10 embodiment, the FIG. 11 embodiment can be provided with a knurled knob and collar (corresponding to the knob 454 and collar 452 of the FIG. 10 embodiment). If such a knob is provided, turning the knob would cause rotation of the entire cannula-insertion device 470 relative to the adapter block 472 about the axis $O_z$ (i.e., about the indicated Z-axis).

The FIG. 11 embodiment 470 can be used to hold any of various tools other than cannulae. For use, the cannula-insertion device 470 is mounted to the controlled end 206 of the manipulator 200 and positioned at a desired location relative to the subject body. Before mounting a cannula (mounted to its respective cannula adapter) to the device 470, a miniature drilling device can be mounted to the respective cannula holder 480, 482 for drilling a hole through which the subject cannula is to be inserted. After drilling the respective hole, the drilling device is detached from the cannula holder and replaced with the respective cannula (in its respective cannula adapter).

The drilling device (or any other tool mounted to a cannula holder 480, 482) desirably is self-indexing in the same manner as the respective cannula adapter 484, 485. Any of various self-indexing tools can thus be attached wherein the terminus of the tool is always situated (whenever the corresponding cannula holder is shifted to its full-down position) at exactly the same position in three-dimensional space. This advantageously avoids having to perform repositioning each time a new tool is mounted to the cannula-insertion device 470.

Based on the previous discussion, it will be appreciated that any of the slide and shift mechanisms of the embodiments of the cannula-insertion devices described above can be substituted with any of various alternative mechanisms. Furthermore, the knurled knobs need not be actuated manually. Rather, it will be immediately apparent that actuation of one or more slide or shift mechanisms can be automated by using motors or the like instead of the knurled knobs.

Figure 13:
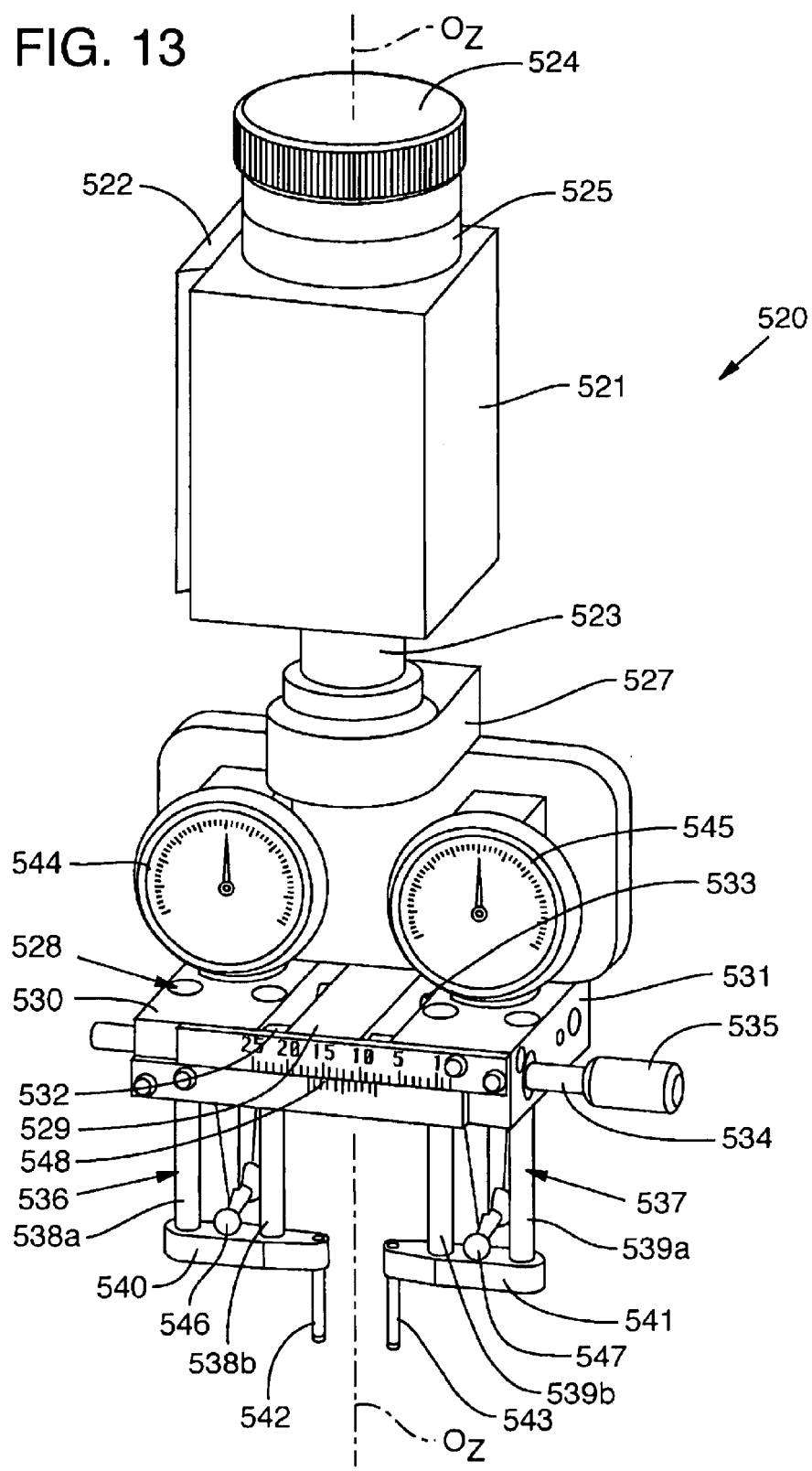
FIG. 13 shows details of a representative embodiment of a stereotaxic alignment indicator as yet another example implement that can be mounted to a manipulator of a stereotaxic alignment system according to the invention.

A sixth example implement is a stereotaxic alignment indicator, of which a representative embodiment 520 is depicted in FIG. 13. When mounted to the controlled end 206 of the manipulator 200, the stereotaxic alignment indicator can provide dimensional feedback to the user required to obtain a desired adjustment/alignment of coronal tilt and dorsal tilt of a body mounted to the stereotaxic holder 10. The embodiment 520 of FIG. 13 comprises a self-indexing adapter block 521, a male dovetail rail segment 522, a shaft 523 inserted into the adapter block 521 and having an axis $O_z$, a knurled knob 524 attached to the shaft 523, and a collar 525. Turning the knurled knob 524 causes rotation of the entire stereotaxic alignment indicator 520 relative to the adapter block 521 about the axis $O_z$. The angular orientation of the stereotaxic alignment indicator 520 about the axis $O_z$ can be locked by tightening a cinching screw (not shown) threaded through the collar 525 to engage the shaft 523.

The shaft 523 is affixed to an angled block 527. On a distal edge of the angled block 527 is mounted a bilateral slide mechanism 528. The bilateral slide mechanism 528 comprises a center block 529 and opposing flanking blocks 530, 531. Parallel guide bars 532, 533 are affixed to and extend bilaterally from the center block 529 through the flanking blocks 530, 531. A threaded shaft 534 (with oppositely pitched threads on each half) extends bilaterally from the center block and is threaded into the flanking blocks 530, 531. Thus, turning a knurled knob 535 attached to an end of the threaded shaft 534 causes the flanking blocks 530, 531 to move synchronously toward or away from the center block 529. To each flanking block 530, 531 is mounted a respective vertical slide mechanism 536, 537. Each vertical slide mechanism comprises a pair of parallel guide bars 538a, 538b and 539a, 539b, respectively. The guide bars slide vertically relative to the respective flanking block 530, 531, and terminate with a respective pin bar 540, 541 affixed to the respective guide bars 538a, 538b and 539a, 539b, respectively. Attached to each pin bar 540, 541 is a respective contact pin 542, 543. Mounted to the angled block 527 are first and second dial indicators 544, 545 for the first and second slide mechanisms 536, 537, respectively. Each of the dial indicators 544, 545 has a stem that extends through the respective flanking block 530, 531 and a respective tip 546, 547 that contacts the respective pin bar 540, 541.

During use, the terminus of each contact pin 542, 543 is placed in contact with the surface of a subject body. Normally, the force of gravity (together with the relatively weak spring bias of the respective tip 546, 547) provides sufficient bias to the pin bars 540, 541 for the respective contact pins 542, 543 to remain in contact with a test surface. The vertical position of one contact pin relative to the other pin can be ascertained by reading the dial indicators 544, 545. I.e., a change in the vertical position of a contact pin 542, 543, causes a corresponding change in the deflection of the respective tip 546, 547. As is generally known with a dial indicator of the type shown, whenever the tip of the dial indicator is displaced a corresponding change is caused in the dimensional value indicated by the dial indicator. In the FIG. 12 embodiment, the tip 546, 547 of each dial indicator 544, 545 contacts the upper surface of the respective pin bar 540, 541. Thus, a change in the vertical position of a contact pin 542, 543 is translated to a change in the vertical position of the respective pin bar 540, 541, thereby changing the dimensional value displayed by the respective dial indicator 544, 545. For ease in calibration, the dial of each dial indicator 544, 545 is adjustable to a desired null value as desired or required. Dial indicators (e.g., LAST WORD™ indicators, model 711-MR, manufactured by Starrett, Athol, Mass.) having an accuracy sufficient for use with rodent skulls desirably have an accuracy of +/−10 μm.

The lateral gap between the contact pins 542, 543 can be adjusted as required by turning the knurled knob 535. The obtained lateral gap is equilateral relative to the axis $O_Z$ (i.e., regardless of the spacing between the pins 542, 543, each pin is an equal distance from the axis $O_Z$). The dimension of the actual gap can be ascertained by consulting a vernier scale 548.

Figure 14A:
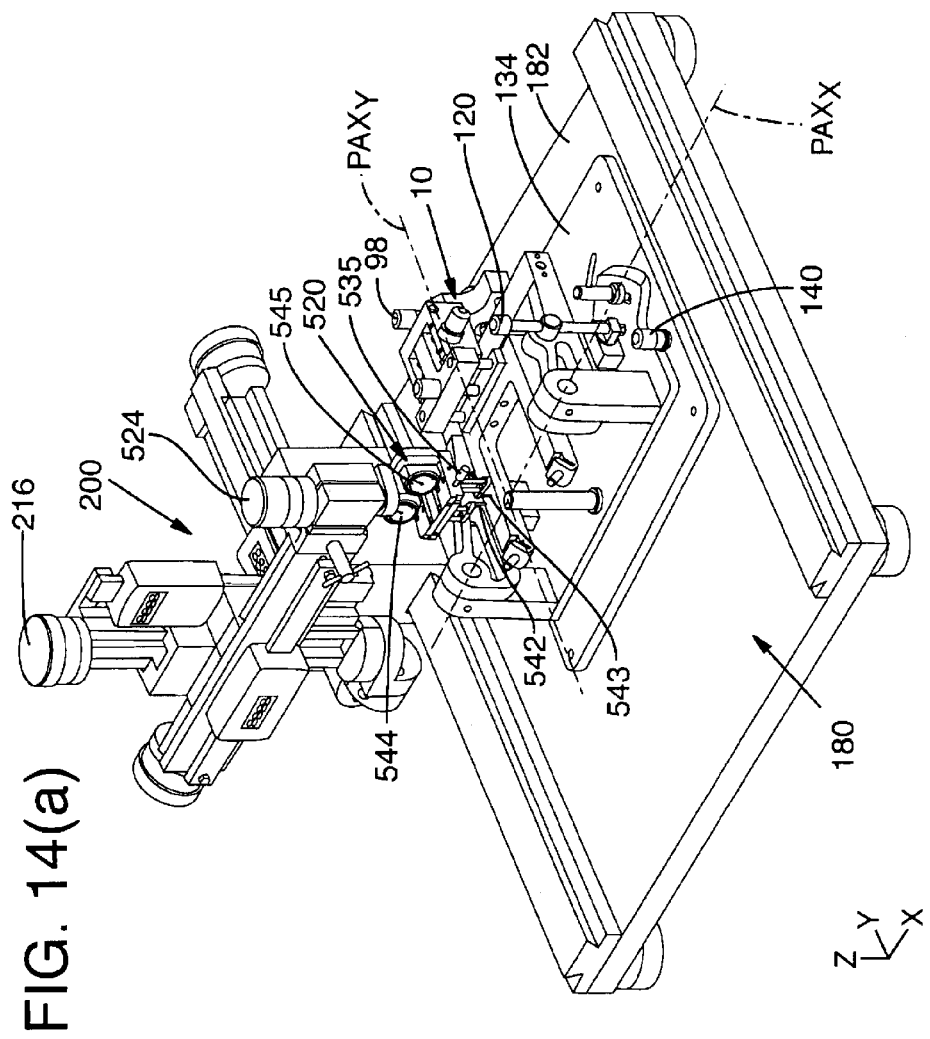
FIG. 14(a) is a front oblique view similar to FIG. 3, but in which a stereotaxic alignment indicator (such as shown in FIG. 13) is mounted to the manipulator rather than the centering scope. The stereotaxic manipulator is oriented to perform a determination of tilt of the subject body about a Y-axis.

During use, the stereotaxic alignment indicator 520 is mounted to the manipulator 200 as described above. Generally, the alignment indicator 520 is first oriented such that a line connecting the termini of the contact pins 542, 543 is parallel with the axis $PAX_X$ of the stereotaxic holder 10, as shown in FIG. 14(a). By turning the knob 216 on the manipulator 200, the alignment indicator 520 is lowered down onto the surface of the subject body structure (e.g., skull, not shown) being held by the stereotaxic holder 10 until the contact pins 542, 543 contact the surface of the body structure. The gap between the contact pins 542, 543 can be adjusted appropriately, by turning the knob 535, to the desired value to contact the desired bilateral loci on the body structure. For example, if the body structure is a rodent skull, then the contact pins 542, 543 can be adjusted to contact bilateral loci flanking the sagittal suture or to correspond with the actual distance between bregma and lambda. To achieve a level aspect of a line extending between the points of contact of the indicator probes with the body structure, the knob 98 of the stereotaxic holder 10 is adjusted, as described above, until both dial indicators 544, 545 read exactly the same value or both indicate a "null" value. Alternatively, adjustment is made to achieve a desired tilt (other than level) of the subject body structure, as indicated on the dial indicators 544, 545.

Figure 14B:
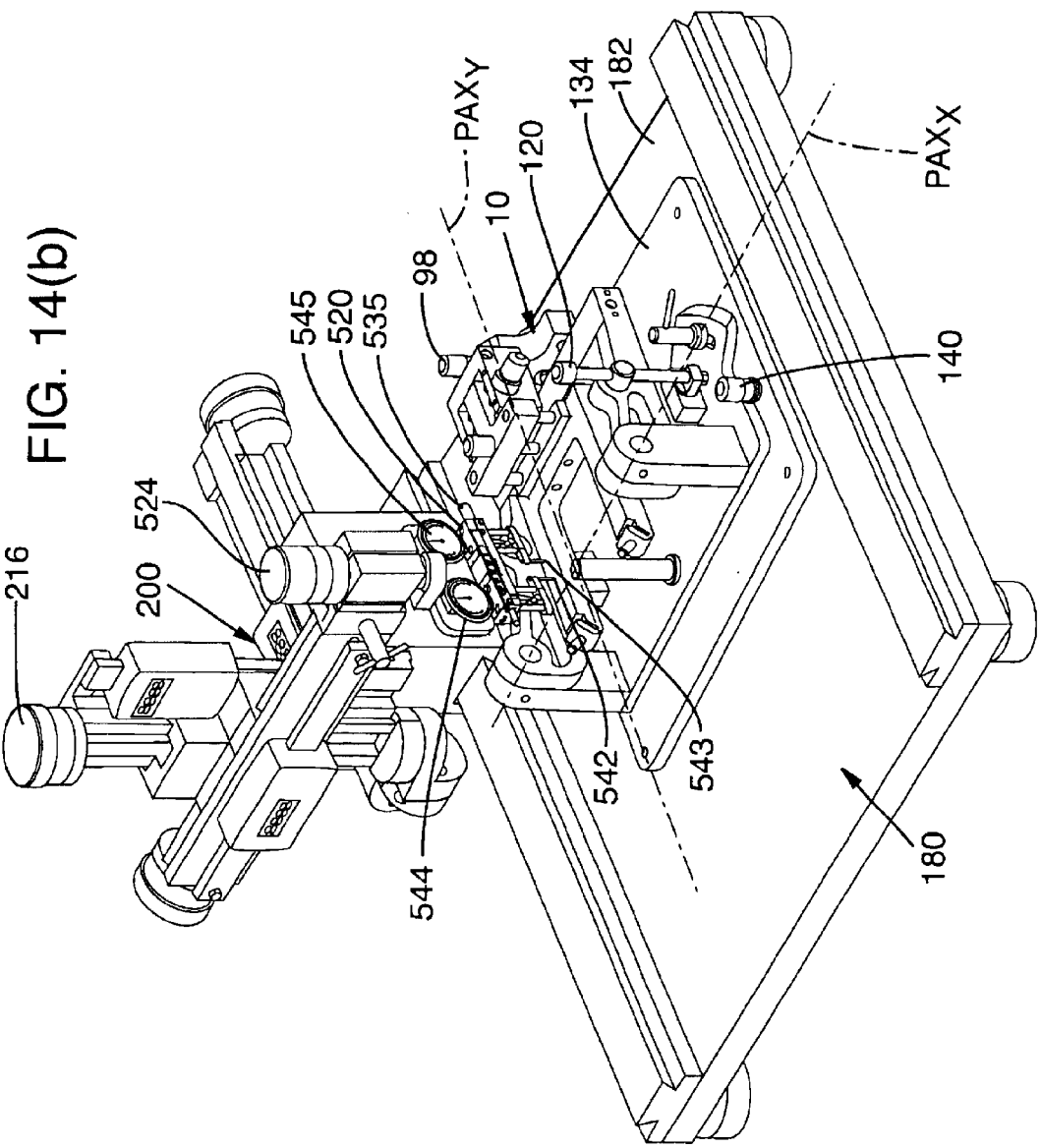
FIG. 14 is a front oblique view similar to FIG. 14(a), but in which the stereotaxic alignment indicator is oriented to perform a determination of tilt of the subject body about an X-axis.

To achieve alignment in the other of the X- and Y-axes, the stereotaxic alignment indicator 520 is raised off the body structure (by turning the knob 216), rotated 90 degrees by turning the knob 524, and lowered again onto the body structure (by turning the knob 216). Thus, a line connecting the termini of the contact pins 542, 543 is now parallel with the axis $PAX_Y$ of the stereotaxic holder 10, as shown in FIG. 14(b). For example, after aligning the sagittal suture of a rodent skull parallel with the $PAX_Y$ axis, the alignment indicator 520 is lowered onto the skull until one of the contact pins 542, 543 contacts bregma and the other contact pin contacts lambda. The knob 120 on the stereotaxic holder 10 is turned to adjust the dorsal tilt of the skull until both dial indicators 544, 545 display the same value or a null value, or a desired differential value. As a result of this adjustment, a line extending between bregma and lambda along the sagittal suture is level or at the desired angular orientation to within, e.g., +/−10 μm.

With respect to an alignment indicator, any of various alternative embodiments to FIG. 13 embodiment are possible. For example, and not intending to be limiting, the dial indicators 544, 545 can be replaced with any of various digital scales, such as those discussed elsewhere herein. Further alternatively, the mechanical vertical slide mechanisms 536, 537 (with associated dial indicators 544, 545) can be replaced with a "touch signal probe" as known in the art or with one or more laser position detectors.

As discussed above, an appropriate snout adapter 160 or other implement for holding a subject body can be attached to the base 14 of the first U-frame 12. (See generally FIG. 1(b) showing a representative embodiment of a snout adapter 160 attached to the mounting rods 152, 154.) An appropriate snout adapter is particularly useful when the subject body is a head or skull. In view of the many differences in skull size and shape among various possible subject animals, the appropriate snout adapter will have a correspondingly different configuration. Snout adapters are used usually in conjunction with other head-holding implements that usually include ear bars 20, 22 as shown in FIGS. 1(a)–1(b). A combination of a snout adapter and ear bars provides a three-point contact system for the subject skull, and three-point contact systems are especially effective for holding the skulls of smaller rodents such as mice, rats, squirrels, and the like. Heads of larger animals such as cats, dogs, and primates frequently need at least one other contact point for adequate stability. For such heads, "eye bars" (that engage the infra-orbital ridge) are used frequently in addition to tooth bars and ear bars. Of course, if the body being held is not a head or skull, the implements used to grasp the body have other respective configurations each of which desirably conforming to a respective anatomical structure so as to provide a stable point of contact.

Figure 15:
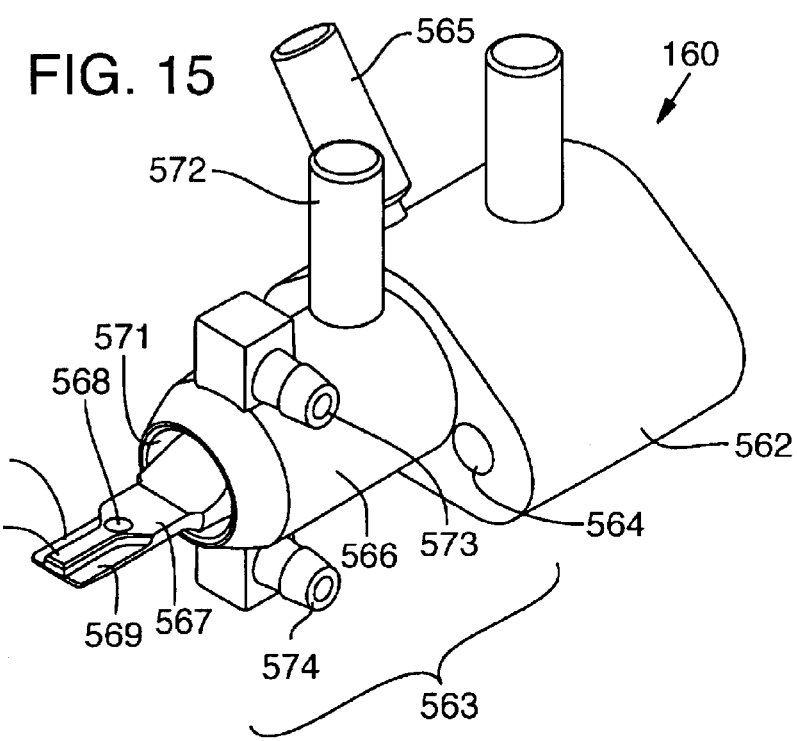
FIG. 15 is a front oblique view of a representative embodiment of a snout adapter that can be mounted to a stereotaxic holder according to the invention.

The embodiment of the snout adapter 160 shown in FIGS. 1(a) and 1(b), which is especially suitable for holding a rodent skull, is detailed in FIG. 15. The FIG. 15 snout adapter 160 is especially suitable for use in conjunction with ear bars, such as the ear bars 20, 22 shown in FIGS. 1(a)–1(b), appropriately sized for the subject skull. The snout adapter 160 comprises a mounting block 562 and a snout-engagement portion 563.

The mounting block 562 defines apertures 564 through which the mounting bars 152, 154 (FIG. 1(b)) extend. A lock screw 565 can be tightened for locking the mounting block 562 at a desired location on the mounting bars 152, 154. Thus, whenever the snout adapter 160 is mounted to the first U-frame 12, the snout adapter 160 is movable relative to the first U-frame 12 substantially along the Y-axis (i.e., to provide a desired anterior-posterior adjustability).

The snout-engagement end 563 comprises a snout-clamp/gas-mask 566 and a palate bar 567. The palate bar 567 defines a through aperture 568 sized to allow the subject's incisors to extend therethrough. The palate bar also defines lateral recesses 569 configured and situated to contact the subject's molars, allowing the subject's palate to rest on a mid-line ridge 570. Whenever the palate bar 567 is thus engaged with the palate of the subject, the snout-clamp/gas-mask 566 can be moved posteriorly relative to the mounting block 562 along the indicated Y-axis to fit over the subject's nose (i.e., the subject's nose is inserted into a cavity 571 defined by the snout-clamp/gas-mask 566), thereby "clamping" the subject's snout. After a desired fit is obtained, a locking screw 572 is tightened. The snout-clamp/gas-mask 566 is also tiltable about the indicated Y-axis, relative to the mounting block 562. The particular tilt can be retained by tightening the locking screw 572.

The snout-clamp/gas-mask 566 also comprises a gas inlet 573 and a gas outlet 574 to allow administration of a gas anesthetic to the subject while the subject's head is engaged in the snout adapter 160. More specifically, the gas inlet 573 is connectable to a supply of anesthetic gas. The gas outlet 574 is connectable, for example, to a waste-gas reservoir maintained under a slight subatmospheric pressure.

As noted above, FIG. 15 shows a representative embodiment of a snout adapter. Any of various other snout adapters as currently known in the art readily can be adapted for mounting to the stereotaxic holder 10. Example conventional snout adapters are available from, for example, Kopf Instruments, Tujunga, Calif. (e.g., model 926 "mouse adapter," model 920 "rat adapter," model 924 "rotational rat adapter," and model 906 "rat anesthesia mask").

Whereas apparatus according to the invention are especially adapted for holding a body (i.e., animal body or portion thereof) for performing a surgical or diagnostic intervention, for example, it will be appreciated that the subject "body" is not limited to animate bodies. In fact, any of various inanimate "bodies" or other workpieces can be held and aligned in a stereotaxic manner using apparatus according to the invention.

A representative protocol for performing a stereotaxic alignment is set forth below as performed using a rodent skull as a representative body structure. In this protocol, it is assumed that the stereotaxic holder 10 and the manipulator 200 are attached to the base 180 as described above. Also, this example protocol is described in the context of the specific embodiments shown in the figures described above. It will be understood that details of the protocol may change with changes, for example, in the specific embodiment that is used and in the particular subject.

(1) If required, the orthogonality of the X-, Y-, and Z-axes of the manipulator 200 are checked. This can be performed, e.g., by mounting the dial test indicator 360 to the controlled end 206 of the manipulator 200, performing "sweeping-in" or "indicating" as described earlier above, and adjusting the jack screws 238, 240, 242 on the universal joint 230 of the manipulator as required.

(2) The dial test indicator 360 is detached from the controlled end 206 and replaced with the centering scope 280. The gauge post 146 is placed on the pad 150. The centering scope 280 is positioned, using the manipulator 200, so that the reticle in the scope is aligned exactly with (and focused on) the centering gauge 148 on the gauge post 146. This action establishes coincidence of the axis $O_Z$ of the centering scope 280 (and thus of the controlled end 206) with the axis $PAX_Z$. Also, by focusing the scope 280 on the centering gauge 148, the point on the $PAX_Z$ axis where the axes $PAX_X$ and $PAX_Y$ cross each other is established. If the manipulator 200 is equipped with digital scales 220, 222, 224, each scale desirably is nulled at this time. In any event, with respect to both the stereotaxic holder 10 and the manipulator 200, a "0,0,0" point is identified in three-dimensional space (i.e., the point where the axes $PAX_X$, $PAX_Y$, $PAX_Z$ orthogonally cross each other). The 0,0,0 point is the reference point from which various loci in or on the subject body are located accurately in three-dimensional space. After the 0,0,0 point is located, the gauge post 146 is removed.

(3) The skull is mounted to the stereotaxic holder 10 using a proper combination of holding implements such as ear bars and snout adapter. If desired, the controlled end 206 of the manipulator can be moved out of the way. The advantage of previously having nulled the scales 220, 222, 224 is immediately apparent because the controlled end 206 can be returned with high accuracy to its previous position simply by adjusting the knobs 214, 216, 218 until all three scales 220, 222, 224 return to their respective null values. In any event, after mounting the skull to the stereotaxic holder 10, the centering scope 280 is returned to the 0,0,0 position and the axis $O_Z$ is made coincident with the $PAX_Z$ axis.

(4) While observing through the centering scope 280, the skull is shifted (using the shift mechanisms 28, 30, 32 as required), to place the desired target feature at the 0,0,0 point (i.e. at the cross-reticle of the centering scope in all three dimensions). For a rodent skull, the target feature is often bregma. However, as noted earlier above, any of various other target features on or in the body can be used, including artificially implanted features.

(5) While still observing through the centering scope 280, a desired anterior-posterior reference line (e.g., a natural linear feature such as the sagittal suture of the skull) is aligned with the Y-direction reticle line in the centering scope. Alternatively, for example, regarding bregma as a first reference point, the centering scope can be shifted (by manipulating the Y-direction shift mechanism 208) to the lambda locus on the skull, and the "swing" of the stereotaxic holder 10 can be adjusted (using the knob 140) as required to align an imaginary anterior-posterior reference line connecting bregma and lambda on the subject skull exactly with the $PAX_Y$ axis.

(6) Using the Y-direction shift mechanism 208, the controlled end 206 is shifted to a position at which the axis $O_Z$ intersects the anterior-posterior line of the skull at midlength, such as midlength between bregma and lambda.

(7) The centering scope 280 is removed, and the stereotaxic alignment indicator 520 is attached to the controlled end 206 of the manipulator 200. Normally, coronal tilt of the subject skull is determined first. This can be done by lowering the contact pins 542, 543 onto respective points on the skull that are located bilaterally relative to the anterior-posterior reference line. The knob 98 on the stereotaxic holder 10 can be adjusted as required to obtain either a level line connecting the two bilateral points or to obtain a line at the desired coronal tilt angle.

(8) The stereotaxic alignment indicator 520 is retracted from the skull (using the Z-axis shift mechanism 210 of the manipulator) sufficiently to allow a 90-degree rotation (using the knob 524) of the alignment indicator 520. Thus, the alignment indicator is positioned for ascertaining the dorsal tilt of the subject skull. The gap between the contact pins 542, 543 is set appropriately (using the knob 535), for example to equal the bregma-lambda distance. The alignment indicator is then lowered until the contact pins 542, 543 contact the skull on the anterior-posterior reference line. The dorsal tilt of the skull is adjusted (by manipulating the knob 34 on the stereotaxic holder 10) until the desired readings (level or otherwise) are obtained on the dial indicators 544, 545. For example, some rodent brain atlases locate features of the brain relative to bregma and lambda being level; other atlases locate features relative to a 2.25-mm offset of bregma to lambda. Either adjustment can be made readily in this step.

Upon completing steps (1)–(8), the subject skull is now positioned in a true stereotaxic plane according to the pertinent reference (brain atlas or other appropriate reference), with a pre-determined degree of confidence based on the accuracy of the indicators (dials, scales, etc.) provided on the apparatus according to the invention. The alignment indicator can be retracted from the skull and replaced with any of various implements attached to the controlled end so as to continue with the surgery or other research intervention involving the subject skull. For example, any of various electrodes, cannulae, probes, etc. can be implanted to desired respective loci within the skull (e.g., within the brain) at a high level of confidence that the desired loci will, in fact, be "hit."

Whereas the invention has been described in connection with representative embodiments, it will be apparent that the invention is not limited to those embodiments. On the contrary, the invention is intended to encompass all modifications, alternatives, and equivalents as may be included within the spirit and scope of the invention, as defined by the appended claims.

What is claimed is:

1. A stereotaxic holder for holding a body at a position in three-dimensional space, comprising:
    a frame to which a body-holding component, configured to contact a body, can be attached such that the body-holding component extends from the frame to contact the body and hold the body relative to the frame;
    an X-axis shift mechanism to which the frame is attached, the X-axis shift mechanism being configured to move the frame, with body-holding component, along an X-axis;
    a Y-axis shift mechanism to which the frame is attached, the Y-axis shift mechanism being configured to move the frame, with body-holding component, along a Y-axis that is orthogonal to the X-axis, the movement along the Y-axis being independent of the movement along the X-axis;
    a Z-axis shift mechanism to which the frame is attached, the Z-axis shift mechanism being configured to move the frame, with body-holding component, along a Z-axis that is orthogonal to both the X-axis and the Y-axis, the movement along the Z-axis being independent of the movement along the X-axis or along the Y-axis and
    at least one tilting mechanism selected from the group consisting of X-axis tilting mechanisms, Y-axis tilting mechanisms, and Z-axis tilting mechanisms;
    the X-axis shift mechanism, Y-axis shift mechanism, and Z-axis shift mechanism being configured relative to each other so as to define a reference X-axis, a reference Y-axis, and a reference Z-axis, respectively, that are orthogonal relative to each other and that mutually intersect at a 0,0,0 point in three-dimensional space, wherein the X-axis shift mechanism, Y-axis shift mechanism, and Z-axis shift mechanism are configured to move a body, mounted to the frame by the body-holding component, as required to place a selected point on or in the body at the 0,0,0 point, and wherein the at least one tilting mechanism is configured to tilt the body, being held by the frame, about the respective reference axis and relative to the 0,0,0 point.

2. The stereotaxic holder of claim 1, comprising at least two of said tilting mechanisms configured to tilt the body, held by the frame, about the respective reference axes and relative to the 0,0,0 point.

3. The stereotaxic holder of claim 1, comprising all three of said tilting mechanisms configured to tilt the body, held by the frame, about the respective reference axes and relative to the 0,0,0 point.

4. The stereotaxic holder of claim 3, wherein the Y-axis tilting mechanism is configured to tilt the body, held by the frame, about the reference Y-axis and relative to the 0,0,0 point, independently of tilting of the body effected by the X-axis tilting mechanism and by the Y-axis tilting mechanism; and
    the Z-axis tilting mechanism is configured to tilt the body, held by the frame, about the reference Z-axis and relative to the 0,0,0 point, independently of tilting of the body effected by the X-axis tilting mechanism and by the Y-axis tilting mechanism.

5. The stereotaxic holder of claim 1, wherein the at least one tilting mechanism is configured to tilt the body, held by the frame, about the respective reference axis and relative to the 0,0,0 point independently of any other tilting motion of the body or of any shifting motion of the frame.

6. The stereotaxic holder of claim 1, further comprising at least one body-holding component attached to the frame.

7. The stereotaxic holder of claim 6, wherein the body-holding component is selected from a group consisting of ear bars and snout adapters.

8. The stereotaxic holder of claim 1, wherein the frame is attached to the Z-axis shifting mechanism, the Z-axis shifting mechanism is attached to the X-axis shifting mechanism, and the X-axis shifting mechanism is attached to the Y-axis shifting mechanism.

9. The stereotaxic holder of claim 8, further comprising a plate, wherein the X-axis tilting mechanism is attached to the plate, the Y-axis shifting mechanism is attached to the X-axis tilting mechanism, the Y-axis tilting mechanism is attached to the Y-axis shifting mechanism, the X-axis shifting mechanism is attached to the Y-axis tilting mechanism, and the Z-axis shifting mechanism is attached to the X-axis shifting mechanism.

10. The stereotaxic holder of claim 9, further comprising a sub-plate, wherein the plate is mounted pivotably to the sub-plate to allow the plate to swing about the reference Z-axis, the plate and sub-plate comprising the Z-axis tilting mechanism.

11. A stereotaxic alignment system, comprising:
a base plate; and
a stereotaxic holder as recited in claim 1 mounted to the base plate.

12. A stereotaxic holder, comprising:
a first U-frame to which a body-holding component, configured to contact a body, can be attached such that the body-holding component extends from the first U-frame to contact and hold the body relative to the first U-frame;
a Z-axis shifting mechanism to which the first U-frame is attached, the Z-axis shifting mechanism being configured to move the first U-frame, with body-holding component, along a Z-axis;
an X-axis shifting mechanism to which the Z-axis shifting mechanism is attached, the X-axis shifting mechanism being configured to move the Z-axis shifting mechanism and first U-frame along an X-axis;
a Y-axis shifting mechanism to which the X-axis shifting mechanism is attached, the Y-axis shifting mechanism being configured to move the X-axis shifting mechanism, Z-axis shifting mechanism, and first U-frame along a Y-axis;
a Y-axis tilting mechanism connecting the X-axis shifting mechanism to the Y-axis shifting mechanism, the Y-axis tilting mechanism defining a reference Y-axis about which the Y-axis tilting mechanism effects tilting of the body; and
an X-axis tilting mechanism and a Z-axis swing mechanism, wherein the Y-axis shifting mechanism is attached to the X-axis tilting mechanism and the X-axis tilting mechanism is attached to the Z-axis swing mechanism, the X-axis tilting mechanism defining a reference X-axis about which the X-axis tilting mechanism effects tilting of the body, and the Z-axis swing mechanism defining a reference Z-axis about which the Z-axis swing mechanism effects a swing of the body, wherein the reference X-axis, reference Y-axis, and reference Z-axis are orthogonal to each other and mutually intersect at a 0,0,0 point in three-dimensional space.

13. The stereotaxic holder of claim 12, wherein the X-axis tilting mechanism comprises a second U-frame having ends that pivot about the reference X-axis and a base to which the Y-axis shifting mechanism is attached.

14. The stereotaxic holder of claim 13, wherein the Z-axis swing mechanism comprises a plate and a sub-plate, wherein the X-axis tilting mechanism is attached to the plate and the plate is attached pivotably to the sub-plate to allow the plate to swing about the reference Z-axis.

15. The stereotaxic holder of claim 12, further comprising at least one body-holding component attached to the first U-frame.

16. The stereotaxic holder of claim 15, wherein the body-holding component is se ected from a group consisting of ear bars and snout adapters.

17. A stereotaxic alignment system, comprising:
a base plate; and
a stereotaxic holder as recited in claim 12 mounted to the base plate.

18. A stereotaxic alignment system, comprising:
(a) a base plate;
(b) a stereotaxic holder mounted to the base plate, the stereotaxic holder comprising (i) a frame to which a body-holding component, configured to contact a body, can be attached such that the body-holding component extends from the frame to contact and hold the body relative to the frame; (ii) an X-axis shift mechanism to which the frame is attached, the X-axis shift mechanism being configured to move the frame, with body-holding component, along an X-axis; (iii) a Y-axis shift mechanism to which the frame is attached, the Y-axis shift mechanism being configured to move the frame, with body-holding component, along a Y-axis that is orthogonal to the X-axis, the movement along the Y-axis being independent of the movement along the X-axis; (iv) and a Z-axis shift mechanism to which the frame is attached, the Z-axis shift mechanism being configured to move the frame, with body-holding component, along a Z-axis that is orthogonal to both the X-axis and the Y-axis, the movement along the Z-axis being independent of the movement along the X-axis or along the Y-axis, wherein the X-axis shift mechanism, the Y-axis shift mechanism, and the Z-axis shift mechanism are configured relative to each other so as to define a reference X-axis, a reference Y-axis, and a reference Z-axis, respectively, that are orthogonal relative to each other and that mutually intersect at a 0,0,0 point in three-dimensional space, wherein the X-axis shift mechanism, Y-axis shift mechanism, and Z-axis shift mechanism are configured to move a body, mounted to the frame by the body-holding component, as required to place a selected point on or in the body at the 0,0,0 point; and
(c) a manipulator mounted to the base plate and comprising a controlled end to which an implement can be mounted, the manipulator being configured to present to the body a tool held by the implement, mounted to the controlled end, at a desired locus on or in the body relative to the 0,0,0 point.

19. The stereotaxic alignment system of claim 18, wherein the stereotaxic holder further comprises at least one tilting mechanism selected from the group consisting of an X-axis tilting mechanism, a Y-axis tilting mechanism, and a Z-axis tilting mechanism, each tilting mechanism being configured to tilt a body, held by the frame, about the respective reference axis and relative to the 0,0,0 point independently of any other tilting motion of the body or of any shifting motion of the frame.

20. The stereotaxic alignment system of claim 18, wherein the stereotaxic holder further comprises a centering gauge indicating the 0,0,0 point.

21. The stereotaxic alignment system of claim 20, further comprising an implement attached to the controlled end, the implement having an alignment axis.

22. The stereotaxic alignment system of claim 21, wherein:
the stereotaxic holder further comprises a centering gauge indicating the 0,0,0 point;
the implement comprises a centering scope having an optical axis coincident with the alignment axis; and
the manipulator is configured to position the centering scope such that the optical axis intersects the centering gauge at the 0,0,0 point.

23. The stereotaxic alignment system of claim 21, wherein the implement is self-indexing relative to the controlled end.

24. The stereotaxic alignment system of claim 18, wherein the manipulator comprises an X-axis shifting mechanism, a Y-axis shifting mechanism, and a Z-axis shifting mechanism for shifting the controlled end along an X-axis, Y-axis, and Z-axis, respectively, relative to the 0,0,0 point.

25. The stereotaxic alignment system of claim 24, wherein the manipulator further comprises a three-axis universal joint to which the X-axis shifting mechanism, the Y-axis shifting mechanism, and Z-axis shifting mechanism are mounted, the universal joint being configured to allow adjustment of an orthogonal relationship of the X-axis, Y-axis, and Z-axis of the manipulator relative to each other.

26. The stereotaxic alignment system of claim 25, wherein the universal joint of the manipulator is further configured to allow adjustment of one or more of the X-axis, Y-axis, and Z-axis of the manipulator with one or more of the reference X-axis, reference Y-axis, and reference Z-axis of the stereotaxic holder.

27. The stereotaxic alignment system of claim 18, wherein the implement is selected from the group consisting of a centering scope, a drilling unit, a syringe holder, a dial test indicator, a cannula-insertion device, and a stereotaxic alignment indicator.

28. A stereotaxic alignment system, comprising:
 (a) a base plate;
 (b) a stereotaxic holder mounted to the base plate, the stereotaxic holder comprising (i) a first U-frame to which a body-holding component, configured to contact a body, can be attached such that the body-holding component extends from the first U-frame to contact and hold the body relative to the first U-frame; (ii) a Z-axis shifting mechanism to which the first U-frame is attached, the Z-axis shifting mechanism being configured to move the first U-frame, with body-holding component, along a Z-axis; (iii) an X-axis shifting mechanism to which the Z-axis shifting mechanism is attached, the X-axis shifting mechanism being configured to move the Z-axis shifting mechanism and first U-frame along an X-axis; (iv) a Y-axis shifting mechanism to which the X-axis shifting mechanism is attached, the Y-axis shifting mechanism being configured to move the X-axis shifting mechanism, Z-axis shifting mechanism, and first U-frame along a Y-axis; (v) a Y-axis tilting mechanism connecting the X-axis shifting mechanism to the Y-axis shifting mechanism, the Y-axis tilting mechanism defining a reference Y-axis about which the Y-axis tilting mechanism effects tilting of the body; and (vi) an X-axis tilting mechanism and a Z-axis swing mechanism, wherein the Y-axis shifting mechanism is attached to the X-axis tilting mechanism and the X-axis tilting mechanism is attached to the Z-axis swing mechanism, the X-axis tilting mechanism defining a reference X-axis about which the X-axis tilting mechanism effects tilting of the body, and the Z-axis swing mechanism defining a reference Z-axis about which the Z-axis swing mechanism effects a swing of the body, wherein the reference X-axis, reference Y-axis, and reference Z-axis are orthogonal to each other and mutually intersect at a 0,0,0 point in three-dimensional space; and
 (c) a manipulator mounted to the base plate and comprising a controlled end to which an implement can be mounted, the manipulator being configured to present to the body a tool held by an implement, mounted to the controlled end, at a desired locus on or in the body relative to the 0,0,0 point.

29. The stereotaxic alignment system of claim 28, wherein each tilting mechanism is configured to tilt a body, held by the frame, about the respective reference axis and relative to the 0,0,0 point independently of any other tilting motion of the body or of any shifting motion of the frame.

30. The stereotaxic alignment system of claim 28, wherein the stereotaxic holder further comprises a centering gauge indicating the 0,0,0 point.

31. The stereotaxic alignment system of claim 30, further comprising an implement attached to the controlled end, the implement having an alignment axis.

32. The stereotaxic alignment system of claim 31, wherein:
 the implement comprises a centering scope having an optical axis that is coincident with the alignment axis and that is positionable at the 0,0,0 point as visualized by an operator using the centering scope; and
 the manipulator is configured to position the centering scope such that the optical axis intersects the 0,0,0 point.

33. The stereotaxic alignment system of claim 31, wherein:
 the sterotaxic holder further comprises a centering gauge indicating the 0,0,0 point;
 the implement comprises a centering scope having an optical axis coincident with the alignment axis; and
 the manipulator is configured to position the centering scope such that the optical axis intersects the centering gauge at the 0,0,0 point.

34. The stereotaxic alignment system of claim 28, wherein the manipulator comprises an X-axis shifting mechanism, a Y-axis shifting mechanism, and a Z-axis shifting mechanism for shifting the controlled end along an X-axis, Y-axis, and Z-axis, respectively, relative to the 0,0,0 point.

35. The stereotaxic alignment system of claim 34, wherein the manipulator further comprises a three-axis universal joint to which the X-axis shifting mechanism, the Y-axis shifting mechanism, and Z-axis shifting mechanism are mounted, the universal joint being configured to allow adjustment of an orthogonal relationship of the X-axis, Y-axis, and Z-axis of the manipulator or relative to each other.

36. The stereotaxic alignment system of claim 35, wherein the universal joint of the manipulator is further configured to allow adjustment of one or more of the X-axis, Y-axis, and Z-axis of the manipulator with one or more of the reference X-axis, reference Y-axis, and reference Z-axis of the stereotaxic holder.

37. The stereotaxic alignment system of claim 28, wherein the implement is selected from the group consisting of a centering scope, a drilling unit, a syringe holder, a dial test indicator, a cannula-insertion device, and a stereotaxic alignment indicator.

38. A method for performing a stereotaxic alignment of a body, comprising:
 providing a reference X-axis, a reference Y-axis, and a reference Z-axis that are orthogonal to each other and that mutually intersect at a 0,0,0 point in three-dimensional space;
 mounting the body in a holder configured to effect respective controlled shifts of the body in an X-axis direction, a Y-axis direction, and a Z-axis direction, and to effect respective controlled tilts of the body about the reference X-axis and reference Y-axis, as well as controlled swings of the body about the reference Z-axis;
 using the holder, shifting the body as required in the X-axis, Y-axis, and Z-axis dimensions to place a selected target point on or in the body at the 0,0,0 point;

using the holder, swinging the body as required about the reference Z-axis while maintaining the target point at the 0,0,0 point, to obtain a desired orientation of the body relative to the reference Y-axis or the reference X-axis;

using the holder, tilting the body as required about the reference Y-axis while maintaining the target point at the 0,0,0 point, to obtain a desired orientation of the body relative to the reference X-axis; and using the holder, tilting the body as required about the reference X-axis while maintaining the target point at the 0,0,0 point, to obtain a desired orientation of the body relative to the reference Y-axis.

39. The method of claim 38, wherein the step of swinging the body about the reference Z-axis comprises the steps of:

identifying a first reference point and a second reference point on or in the body, the first and second reference points defining a reference line; and swinging the body as required about the reference Z-axis until the reference line is at a desired orientation relative to the reference X-axis or the reference Y-axis.

40. The method of claim 39, wherein:

the reference line is a sagittal axis of the body; and placing the reference line at the desired orientation achieves a sagittal alignment of the body.

41. The method of claim 38, wherein the step of tilting the body about the reference Y-axis comprises the steps of:

providing a stereotaxic alignment indicator for ascertaining the orientation of the body relative to the reference X-axis;

placing the stereotaxic alignment indicator into functional contact with the body; and tilting the body as required until the stereotaxic alignment indicator indicates the desired orientation of the body about the reference Y-axis relative to the reference X-axis.

42. The method of claim 41, wherein:

the body is aligned to have its sagittal axis aligned with the reference Y-axis; and obtaining the desired orientation of the body about the reference Y-axis places the body at a desired coronal tilt.

43. The method of claim 41, wherein, in the step of tilting the body, the body is tilted to cause the stereotaxic alignment indicator to provide a data output corresponding to the orientation of the body.

44. The method of claim 38, wherein the step of tilting the body about the reference X-axis comprises the steps of:

providing a stereotaxic alignment indicator for ascertaining the orientation of the body relative to the reference Y-axis;

placing the stereotaxic alignment indicator into functional contact with the body; and tilting the body as required until the stereotaxic alignment indicator indicates the desired orientation of the body about the reference X-axis relative to the reference Y-axis.

45. The method of claim 44, wherein:

the body is aligned to have its sagittal axis aligned with the reference Y-axis; and obtaining the desired orientation of the body about the reference X-axis places the body at a desired dorsal tilt.

46. The method of claim 44, wherein, in the step of tilting the body, the body tilted to cause the stereotaxic alignment indicator to provide a data output corresponding to the orientation of the body.

47. A stereotaxic holder for holding a body at a position in three-dimensional space, comprising:

a frame to which a body-holding component can be attached such that the body-holding component, mounted to the frame, contacts the body and holds the body relative to the frame;

an X-axis tilting mechanism, a Y-axis tilting mechanism, a Z-axis tilting mechanism, and a shift mechanism, to which mechanisms the frame is coupled;

the X-axis tilting mechanism being configured to tilt the body, held to the frame by the body-holding component, about a reference X-axis;

the Y-axis tilting mechanism being configured to tilt the body, held to the frame by the body-holding component, about a reference Y-axis;

the Z-axis tilting mechanism being configured to pivot the body, held to the frame by the body-holding component, about a reference Z-axis;

the reference X-axis, reference Y-axis, and reference Z-axis being orthogonal to each other and mutually intersecting at a 0,0,0 point in three-dimensional space; and the shift mechanism being configured to move the body, mounted to the frame by the body-holding component, to place a selected point on or in the body at the 0,0,0 point.

48. The stereotaxic holder of claim 47, wherein each of the X-axis tilting mechanism, the Y-axis tilting mechanism, and the Z-axis tilting mechanism tilts the body, held to the frame by the body-holding component, about the respective reference axis in a manner that is independent of tilting of the other two tilting mechanisms.

49. The stereotaxic holder of claim 47, wherein the shift mechanism comprises at least one of an X-axis shift mechanism, a Y-axis shift mechanism, and a Z-axis shift mechanism.

50. The stereotaxic holder of claim 47, wherein the shift mechanism comprises an X-axis shift mechanism configured to move the frame, with body-holding component, along an X-axis.

51. The stereotaxic holder of claim 50, wherein the shift mechanism further comprises a Z-axis shift mechanism configured to move the frame, with body-holding component and independently of the X-axis shift mechanism, along a Z-axis that is orthogonal to the X-axis.

52. The stereotaxic holder of claim 50, wherein the shift mechanism further comprises a Y-axis shift mechanism configured to move the frame, with body-holding component and independently of the X-axis shift mechanism, along a Y-axis that is orthogonal to the X-axis.

53. The stereotaxic holder of claim 52, wherein the shift mechanism further comprises a Z-axis shift mechanism configured to move the frame, with body-holding component and independently of the X-axis and Y-axis shift mechanisms, along a Z-axis that is orthogonal to the X-axis and Y-axis.

54. The stereotaxic holder of claim 47, wherein the shift mechanism comprises a Y-axis shift mechanism configured to move the frame, with body-holding component, along a Y-axis.

55. The stereotaxic holder of claim 47, wherein the shift mechanism comprises a Z-axis shift mechanism configured to move the frame, with body-holding component, along a Z-axis.

56. The stereotaxic holder of claim 47, wherein the shift mechanism comprises:
   an X-axis shift mechanism configured to move the frame, with body-holding component, along an X-axis that is parallel to the reference X-axis;
   a Y-axis shift mechanism configured to move the frame, with body-holding component, along a Y-axis that is orthogonal to the X-axis and parallel to the reference Y-axis; and
   a Z-axis shift mechanism configured to move the frame, with body-holding component, along a Z-axis that is orthogonal to the X- and Y-axes and parallel to the reference Z-axis.

57. The stereotaxic holder of claim 47, wherein each of the tilting mechanisms configured to tilt the body, held to the frame by the body-holding component, about the respective reference axis and relative to the 0,0,0 point, independently of any other tilting motion of the body or o any shifting motion of the frame.

58. A stereotaxic alignment system, comprising:
   a base plate; and
   a stereotaxic holder as recited in claim 47 mounted to the base plate.

59. A stereotaxic alignment system, comprising:
   a base plate;
   a stereotaxic holder mounted to the base plate, the stereotaxic holder comprising (a) a frame to which a body-holding component can be attached such that the body-holding component, mounted to the frame, contacts the body and holds the body relative to the frame; (b) an X-axis tilting mechanism, a Y-axis tilting mechanism, a Z-axis tilting mechanism, and a shift mechanism, to which mechanisms the frame is coupled, wherein (i) the X-axis tilting mechanism is configured to tilt the body, held to the frame by the body-holding component, about a reference X-axis, (ii) the Y-axis tilting mechanism is configured to tilt the body, held to the frame by the body-holding component, about a reference Y-axis, (iii) the Z-axis tilting mechanism is configured to pivot the body, held to the frame by the body-holding component, about a reference Z-axis; (iv) the reference X-axis, reference Y-axis, and reference Z-axis are orthogonal to each other and mutually intersecting at a 0,0,0 point in three-dimensional space; and (v) the shift mechanism is configured to move the body, mounted to the frame by the body-holding component, to place a selected point on or in the body at the 0,0,0 point; and
   a manipulator mounted to the base plate and comprising a controlled end to which an implement can be mounted, the manipulator being configured to present to the body a tool held by the implement, mounted to the controlled end, at a desired locus on or in the body relative to the 0,0,0 point.

60. The stereotaxic alignment system of claim 59, wherein each tilting mechanism is configured to tilt a body, held by the frame, about the respective reference axis and relative to the 0,0,0 point independently of any other tilting motion of the body or of any shifting motion of the frame.

61. The stereotaxic alignment system of claim 59, wherein the shift mechanism comprises at least one of an X-axis shift mechanism, a Y-axis shift mechanism, and a Z-axis shift mechanism.

62. The stereotaxic alignment system of claim 59, wherein the stereotaxic holder further comprises a centering gauge indicating the 0,0,0 point.

63. The stereotaxic alignment system of claim 59, further comprising an implement attached to the controlled end, the implement having an alignment axis.

64. The stereotaxic alignment system of claim 59, wherein the manipulator comprises an X-axis shifting mechanism, a Y-axis shifting mechanism, and a Z-axis shifting mechanism for shifting the controlled end along an X-axis, Y-axis, and Z-axis, respectively, relative to the 0,0,0 point.

65. The stereotaxic alignment system of claim 64, wherein the manipulator further comprises a three-axis universal joint to which the X-axis shifting mechanism, the Y-axis shifting mechanism, and Z-axis shifting mechanism are mounted, the universal joint being configured to allow adjustment of an orthogonal relationship of the X-axis, Y-axis, and Z-axis of the manipulator relative to each other.

66. The stereotaxic alignment system of claim 65, wherein the universal joint further configured to allow adjustment of one or more of the X-axis, Y-axis, and Z-axis of the manipulator with one or more of the reference X-axis, reference Y-axis, and reference Z-axis of the stereotaxic holder.

67. The stereotaxic alignment system of claim 66, wherein:
   the implement comprises a centering scope having an optical axis that is coincident with the alignment axis and that is positionable at the 0,0,0 point as visualized by an operator using the centering scope; and
   the manipulator is configured to position the centering scope such that the optical axis intersects the 0,0,0 point.

68. The stereotaxic alignment system of claim 66, wherein:
   the stereotaxic holder further comprises a centering gauge indicating the 0,0,0 point;
   the implement comprises a centering scope having an optical axis coincident with the alignment axis; and
   the manipulator is configured to position the centering scope such that the optical axis intersect the centering gauge at the 0,0,0 point.

69. The stereotaxic alignment system of claim 66, wherein the implement is self-indexing relative to the controlled end.

70. The stereotaxic alignment system of claim 59, wherein the implement is selected from the group consisting of a centering scope, a drilling unit, a syringe holder, a dial test indicator, a cannula-insertion device, and a stereotaxic alignment indicator.

71. A method for performing a stereotaxic alignment of a body, comprising:
   establishing a0,0,0 point representing a mutual intersection point, in three-dimensional space, of a reference X-axis, a reference Y-axis, and a reference Z-axis that are orthogonal to each other;
   shifting the body as required along one or more of an X-axis, a Y-axis, and a Z-axis as required to place a selected target point on or in the body at the 0,0,0 point;
   while maintaining the target point at the 0,0,0 point, tilting the body about the reference Z-axis to obtain a desired orientation of the body relative to the reference X-axis or reference Y-axis;
   while maintaining the target point at the 0,0,0 point, tilting the body about the reference Y-axis to obtain a desired orientation of the body relative to the reference X-axis; and
   while maintaining the target point at the 0,0,0 point, tilting the body about the reference X-axis to obtained a desired orientation of the body relative to the reference Y-axis.

* * * * *

UNITED STATES PATENT AND TRADEMARK OFFICE
CERTIFICATE OF CORRECTION

PATENT NO. : 6,716,220 B2
DATED : April 6, 2004
INVENTOR(S) : Saracione

It is certified that error appears in the above-identified patent and that said Letters Patent is hereby corrected as shown below:

Column 1,
Line 4, omission of acknowledgement of Government support should read:
-- ACKNOWLEDGEMENT OF GOVERNMENT SUPPORT
Work leading to this invention was supported under Grant No. 2R44NS37523-2 from the National Institute of Neurological Disorders and Stroke, National Institutes of Health. The U.S. government has certain rights in this invention. --.

Column 2,
Line 59, "system." should read -- system). --.

Column 7,
Line 16, "FIG. 14 is" should read -- FIG. 14(b) is --.

Column 20,
Line 37, "to FIG. 13 embodiment" should read -- to the FIG.-13 embodiment --.

Column 25,
Line 62, "se ected" should read -- selected --.

Column 31,
Line 17, "or o any" should read -- or of any --.

UNITED STATES PATENT AND TRADEMARK OFFICE
CERTIFICATE OF CORRECTION

PATENT NO. : 6,716,220 B2
DATED : April 6, 2004
INVENTOR(S) : Saracione

It is certified that error appears in the above-identified patent and that said Letters Patent is hereby corrected as shown below:

Column 32,
Line 14, "universal joint further" should read -- universal joint of the manipulator is further --.
Line 35, "axis intersect the" should read -- axis intersects the --.
Line 46, "a0,0,0 point" should read -- a 0,0,0 point --.
Line 63, "to obtained a" should read -- to obtain a --.

Signed and Sealed this

Twenty-sixth Day of April, 2005

JON W. DUDAS
*Director of the United States Patent and Trademark Office*